United States Patent
McNeel et al.

(10) Patent No.: US 10,191,056 B2
(45) Date of Patent: *Jan. 29, 2019

(54) DIAGNOSTIC EVALUATION OF ANTIBODY RESPONSES TO COMMONLY RECOGNIZED PROSTATE CANCER-ASSOCIATED ANTIGENS

(71) Applicant: Wisconsin Alumni Research Foundation, Madison, WI (US)

(72) Inventors: Douglas G. McNeel, Madison, WI (US); Brett B. Maricque, Green Bay, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/757,607

(22) Filed: Dec. 23, 2015

(65) Prior Publication Data
US 2016/0238606 A1    Aug. 18, 2016

Related U.S. Application Data

(63) Continuation of application No. 13/088,594, filed on Apr. 18, 2011.

(60) Provisional application No. 61/324,953, filed on Apr. 16, 2010.

(51) Int. Cl.
| | | |
|---|---|---|
| *C40B 40/10* | (2006.01) | |
| *G01N 33/574* | (2006.01) | |
| *G01N 33/531* | (2006.01) | |

(52) U.S. Cl.
CPC ....... *G01N 33/57434* (2013.01); *C40B 40/10* (2013.01); *G01N 33/531* (2013.01); *G01N 2800/60* (2013.01)

(58) Field of Classification Search
None
See application file for complete search history.

(56) References Cited

U.S. PATENT DOCUMENTS

| | | | | |
|---|---|---|---|---|
| 4,208,479 A | * | 6/1980 | Zuk | C07J 41/0016 435/7.72 |
| 7,635,753 B2 | * | 12/2009 | McNeel | G01N 33/5743 530/350 |
| 2008/0206289 A1 | * | 8/2008 | McNeel | G01N 33/5743 424/277.1 |

FOREIGN PATENT DOCUMENTS

| | | |
|---|---|---|
| WO | WO2000000824 | 1/2000 |
| WO | WO2008103645 A2 | 8/2008 |
| WO | WO2011130742 A3 | 12/2011 |

OTHER PUBLICATIONS

Maricque et al. (The Prostate Jul. 14, 2010, 71: 134-146).*
Macmillan Dictionary (Kit, http://www.macmillandictionary.com/dictionary/american/kit, retrieved Aug. 23, 2013).*
Morse and McNeel (Human Immunology, Mar. 5, 2010, 71:496-504).*
Benjamini et al. "Controlling the False Discovery Rate: A Practical and Powerful Approach to Multiple Testing" J. Roy. Stat. Soc. B vol. 57, 1995, pp. 289-300.
Bradford, T. et al., "Cancer immunomics: using autoantibody signatures in the early detection of prostate cancer," Urol. Oncol. 24:237-242 (2006).
Brinkmann, U., et al., "Novel genes in the PAGE and GAGE family of tumor antigens found by homology walking in the dbEST database," Cancer Res. 59:1445-1448 (1999).
Chen, M., et al., Isolation and characterization of PAGE-1 and GAGE-7. New genes expressed in the LNCaP prostate cancer progression model that share homology with melanoma-associated antigens, J. Biol. Chem. 273:17618-17625 (1998).
Chen, Y., et al., "A testicular antigen aberrantly expressed in human cancers detected by autologous antibody screening," Proc. Natl. Acad. Sci. USA 94:1914-1918 (1997).
Chen, Y., et al., "Identification of multiple cancer/testis antigens by allogeneic antibody screening of a melanoma cell line library," Proc Natl Acad Sci USA 95:6919-6923 (1998).
Crew, A., et al., "Fusion of SYT to two genes, SSX1 and SSX2, encoding proteins with homology to the Kruppel-associated box in human synovial sarcoma," Embo. J. 14:2333-2340 (1995).
De Marzo, A.M. et al., "Proliferative Inflammatory Atrophy of the Prostate : Implications for Prostatic Carcinogenesis", Am. J. Pathol. vol. 155, No. 6, 1999, pp. 1985-1992.
De Plaen, E., et al., "Structure, chromosomal localization, and expression of 12 genes of the MAGE family," Immunogenetics 40:360-369 (1994).
Dennis, L.K. et al, "Epidemiologic association between prostatitis and prostate cancer", Urology vol. 60,No. 1, 2002, pp. 78-83.
Dong, X., et al., "Identification of two novel CT antigens and their capacity to elicit antibody response in hepatocellular carcinoma patients," Br. J. Cancer 89:291-297 (2003).
Dubovsky, J.A. & D.G. McNeel, "Inducible expression of a prostate cancer-testis antigen, SSX-2, following treatment with a DNA methylation inhibitor", Prostate vol. 67, No. 16,, 2007, pp. 1781-1790.
Dubovsky, J.A. et al., "MAD-CT-2 Identified as a Novel Melanoma Cancer-testis Antigen Using Phage Immunoblot Analysis", J. Immunother. vol. 30,No. 7, 2007, pp. 675-683.
Zendman, A., et al., "CTp11, a novel member of the family of human cancer/testis antigens," Cancer Res. 59:6223-6229 (1999).
Dunphy et al., "Antigen-Specific IgG Elicited in Subjects with Prostate Cancer Treated with Flt3 Ligand" J. Immunother vol. 28, No. 3, 2005, pp. 268-275.
Dunphy, E. J. et al., "Identification of Antigen-Specific IgG in Sera from Patients with Chronic Prostatitis", Journal of Clinical Immunology, vol. 24, No. 5, pp. 492-502 (2004).

(Continued)

*Primary Examiner* — Peter J Reddig
(74) *Attorney, Agent, or Firm* — Quarles & Brady LLP

(57) ABSTRACT

The present invention relates to a plurality of antigens that together form a panel of immunoreactive molecules suitable for identifying candidates for prostate cancer examination. Methods for identifying antibodies indicative of a premalignant or malignant prostate are disclosed. Further disclosed are kits that can be used to practice the above methods.

6 Claims, 17 Drawing Sheets

Specification includes a Sequence Listing.

(56) References Cited

OTHER PUBLICATIONS

Dunphy, E.J. et al., "New approaches to identification of antigenic candidats for future prostate cancer immunotherapy", Update on Cancer Therapeutics, vol. I, pp. 273-284, 2006.

Fossa et al., "Identification of nucleolar protein No55 as a tumour-associated autoantigen in patients with prostate cancer" Br. J. Cancer vol. 83,No. 6, 2000, pp. 743-749.

Gilardoni et al. "Prostate cancer induction in autoimmune rats and modulation of T cell apoptosis" J. Exp. Clin. Cancer Res. vol. 18, 1999, pp. 493-504.

Greene et al., "Prostate Specific Antigen Best Practice Statement: 2009 Update", J Urol vol. 182, issue 5, 2009, pp. 2232-2241.

Gure, A., et al., "SSX: a multigene family with several members transcribed in normal testis and human cancer," Int. J. Cancer 72:965-971 (1997).

Hoeppner, L.H. et al., "Humoral immune responses to testis antigens in sera from patients with prostate cancer", Cancer Immunity, vol. 6, No. 1, pp. 1-11, 2006.

Jemal, A. et al., "Cancer Statistics, 2009", CA Cancer J. Clin. vol. 59, issue 4, pp. 225-249, 2009.

Kasahara, M., et al., "A testis-specific gene Tpx-1 maps between Pgk-2 and Mep-1 on mouse chromosome 17," Immunogenetics 29:61-63 (1989).

Kindt et al.: 'Kuby Immunology', 2006 p. 574.

Lee, S., et al., "Immunomic analysis of human sarcoma," Proc Natl Acad Sci USA 100:2651-2656 (2003).

Lim, S., et al., "Sperm protein 17 is a novel cancer-testis antigen in multiple myeloma," Blood 97:1508-1510 (2001).

Loriot, A., et al., "Five new human cancer-germline genes identified among 12 genes expressed in spermatogonia," Int J. Cancer 105:371-376 (2003).

Lurquin, C., et al., "Two members of the human MAGEB gene family located in Xp21.3 are expressed in tumors of various histological origins," Genomics 46:397-408 (1997).

Maricque, B.B., et al., "Antibody response to prostate-associated antigens in patients with prostatis and prostate cáncer", The Prostate, vol. 71, pp. 134-146, 2011.

McDowell, K.A. et al."Leukocytic promotion of prostate cellular proliferation", Prostate vol. 70,No. 4, 2010, pp. 377-389.

McNeel, D., et al., "Antibody immunity to prostate cancer associated antigens can be detected in the serum of patients with prostate cancer," J. Urol. 164:1825-1829 (2000).

Mercader et al.,"T cell infiltration of the prostate induced by androgen withdrawal in patients with prostate cancer", Proc. Nat. Acad. Sci. vol. 98, No. 25, 2001, pp. 14565-14570.

Mooney, C., et al., "Identification of autoantibodies elicited in a patient with prostate cancer presenting as dermatomyositis," Inter. J. Urology 13:211-217 (2006).

Morse et al., "Prostate cancer patients on androgen deprivation therapy develop persistent changes in adaptive immune responses" Hum. Immunol. 71:496-504 (2010).

Narayanan et al., "Inflammatory processes of prostate tissue microenvironment drive rat prostate carcinogenesis: Preventive effects of celecoxib", Prostate vol. 69, No. 2, 2009, pp. 133-141.

Olson,B.M. and D.G. McNeel, "Antibody and T-cell responses specific for the androgen receptor in patients with prostate cancer", Prostate vol. 67, No. 16, 2007, pp. 1729-1739.

Palapattu et al., "Prostate carcinogenesis and inflammation: emerging insights", Carcinogenesis vol. 26,No. 7, 2005, pp. 1170-1181.

Sahin et al., "Human neoplasms elicit multiple specific immune responses in the autologous host" Proc. Nat. Acad. Sci. vol. 92,No. 25, 1995, pp. 11810-11813.

Sasaki, M., et al., "MAGE-E1, a new member of the melanoma-associated antigen gene family and its expression in human glioma," Cancer Res. 61:4809-4814 (2001).

Scanlan, M., et al., "Identification of cancer/testis genes by database mining and mRNA expression analysis," Int. J. Cancer 98:485-492 (2002).

Scanlan, M.J. et al., "The Cancer/Testis Genes: Review, Standarization, and Commentary", Cancer Immunity, vol. 1, No. 1, pp. 1-15, 2004.

Sfanos, K.S. et al.,"Human prostate-infiltrating CD8+ T lymphocytes are oligoclonal and PD-1+", Prostate vol. 69, No. 15, 2009, pp. 1694-1703.

Smith, H.E, et al., "IgG response to tissue -associated antigens as biomarkers of immunological treatment efficacy", Journal of Biomedicine and Biotechnology, vol. 2011, pp. 1-10.

Thompson, I.M., et al., "The influence of finasteride on the development of prostate cancer", New Eng. Journal of Medicine, vol. 349, No. 3, pp. 215-224, 2003.

Van Den Eynde, B., et al., "A new family of genes coding for an antigen recognized by autologous cytolytic T lymphocytes on a human melanoma," J. Exp. Med. 182:689-698 (1995).

Van Der Bruggen, P., et al., "A gene encoding an antigen recognized by cytolytic T lymphocytes on a human melanoma," Science 254:1643-1647 (1991).

Wang, X., et al., "Autoantibody signatures in prostate cancer," N. Engl. J. Med. 353:1224-1235 (2005).

Yuan, L., et al., "Isolation of a novel gene, TSP50, by a hypomethylated DNA fragment in human breast cancer," Cancer Res. 59:3215-3221 (1999).

* cited by examiner

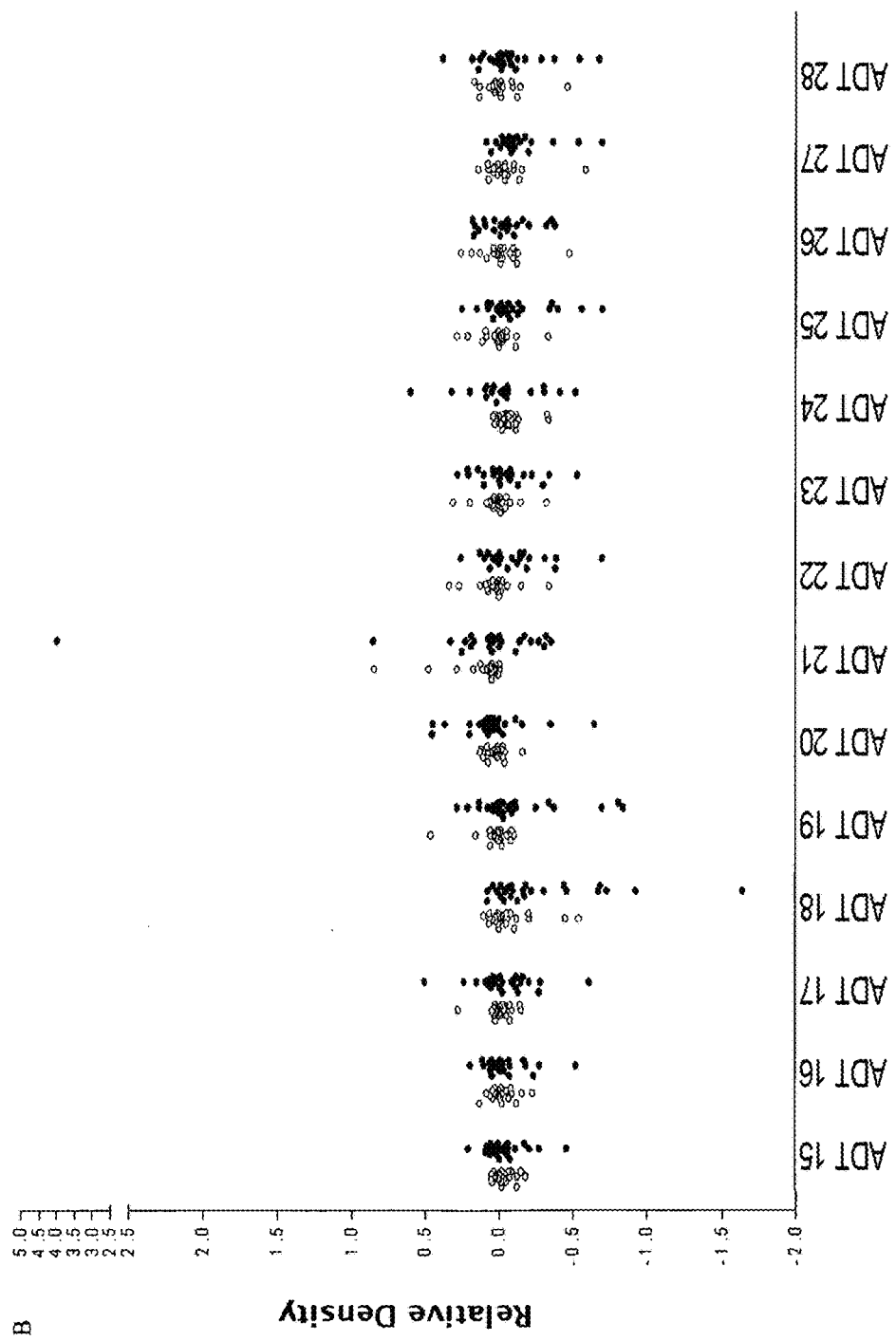
FIGS. 2A-2H, CONT'D.

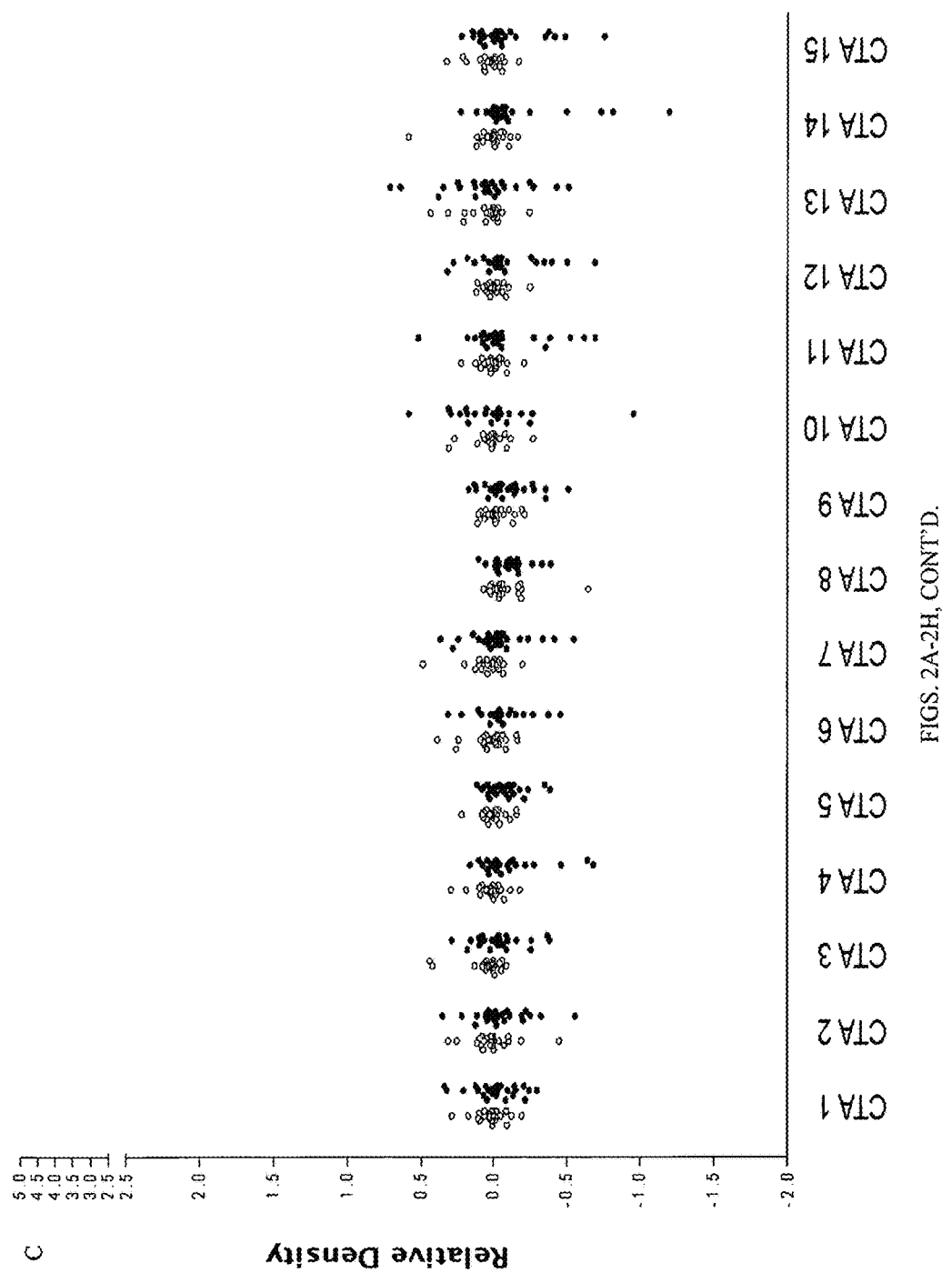
FIGS. 2A-2H, CONT'D.

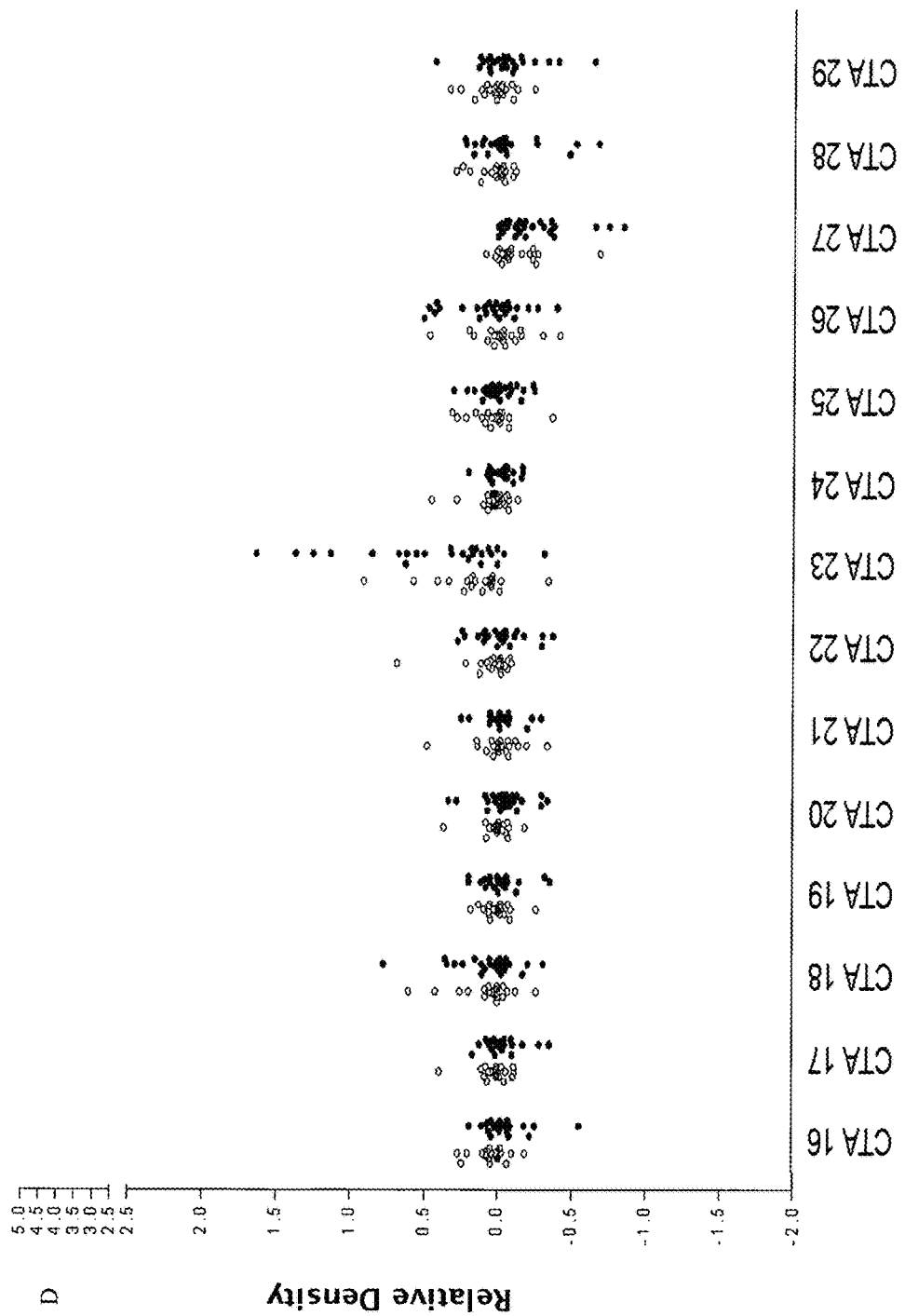
FIGS. 2A-2H, CONT'D.

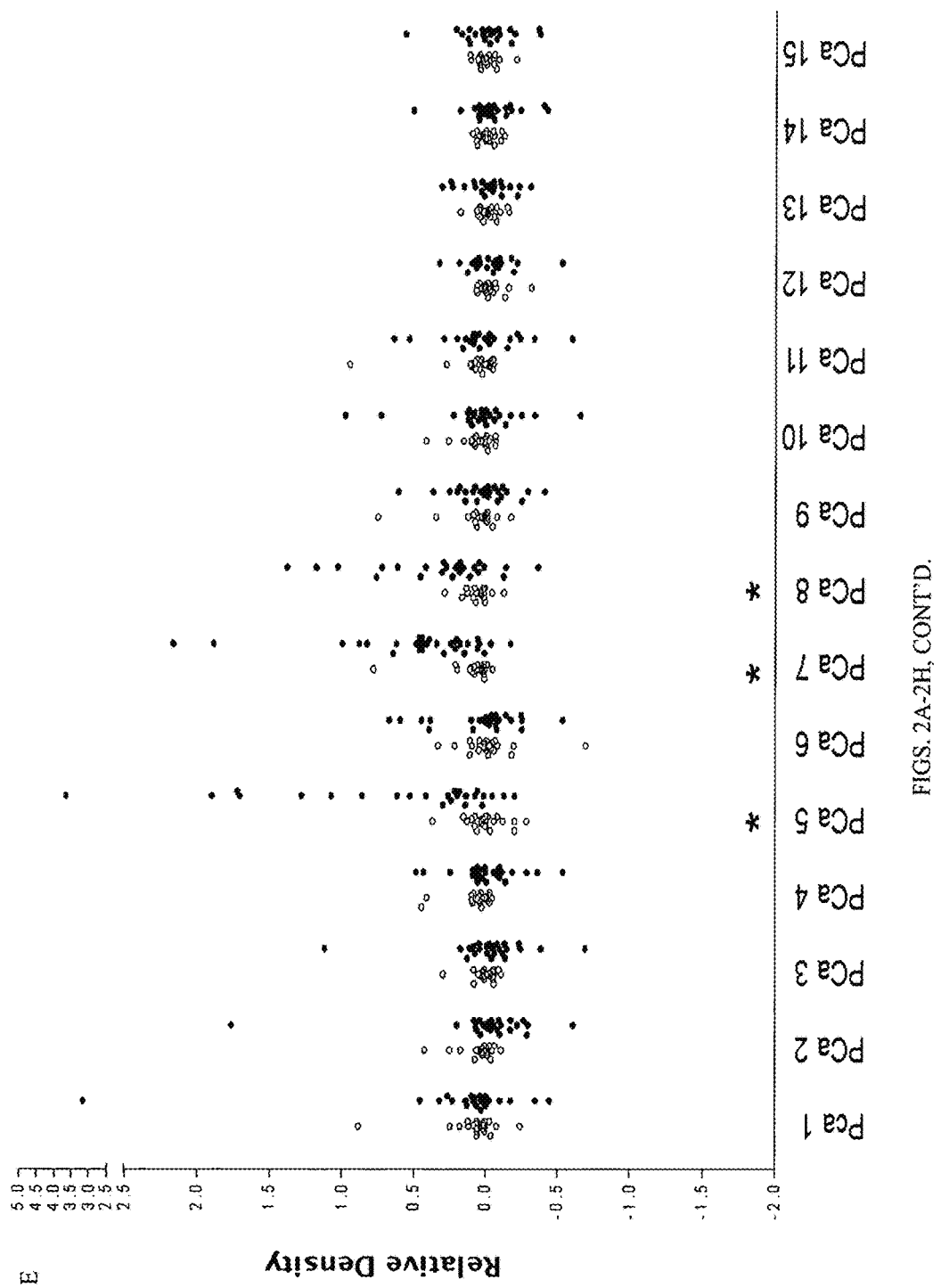
FIGS. 2A-2H, CONT'D.

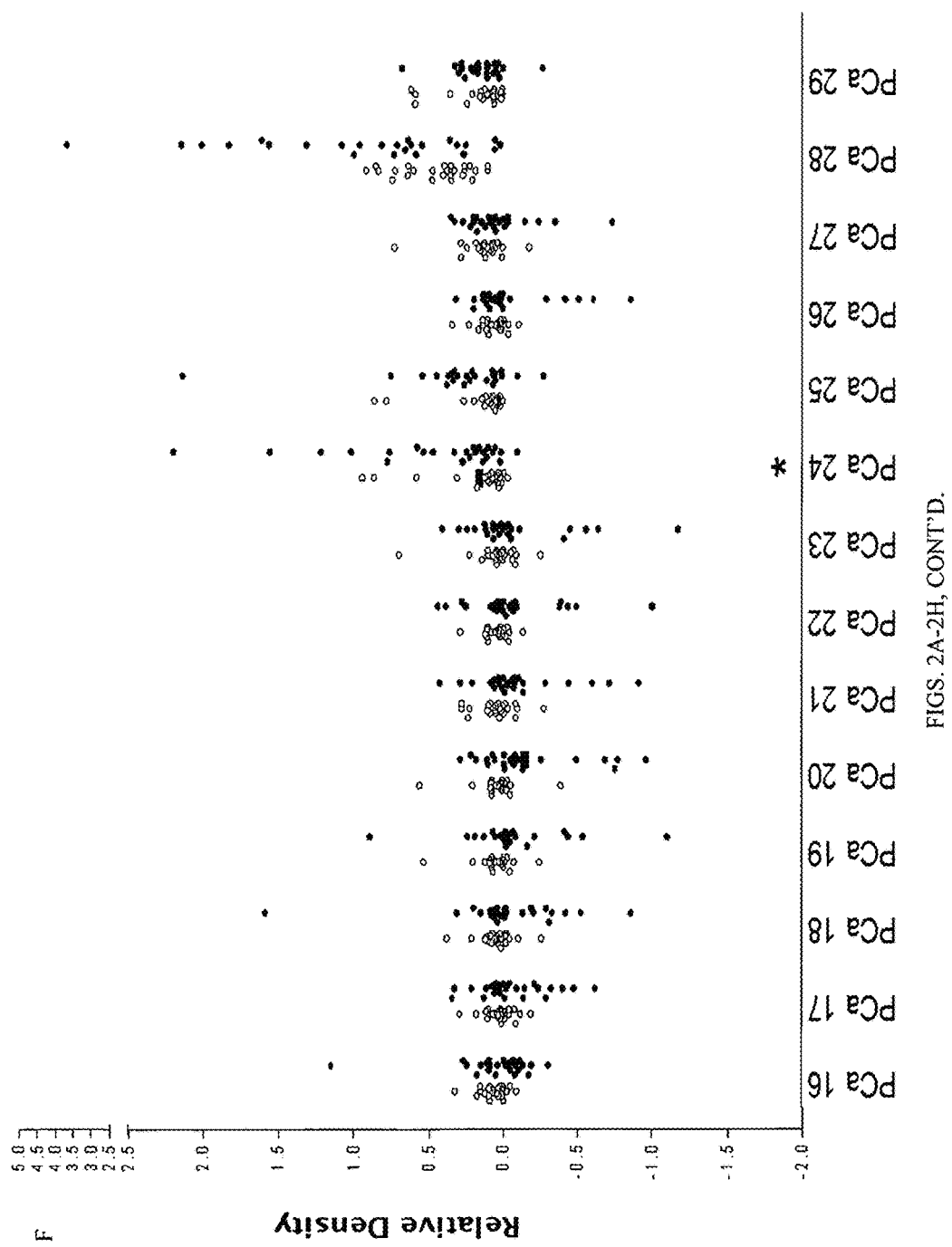
FIGS. 2A-2H, CONT'D.

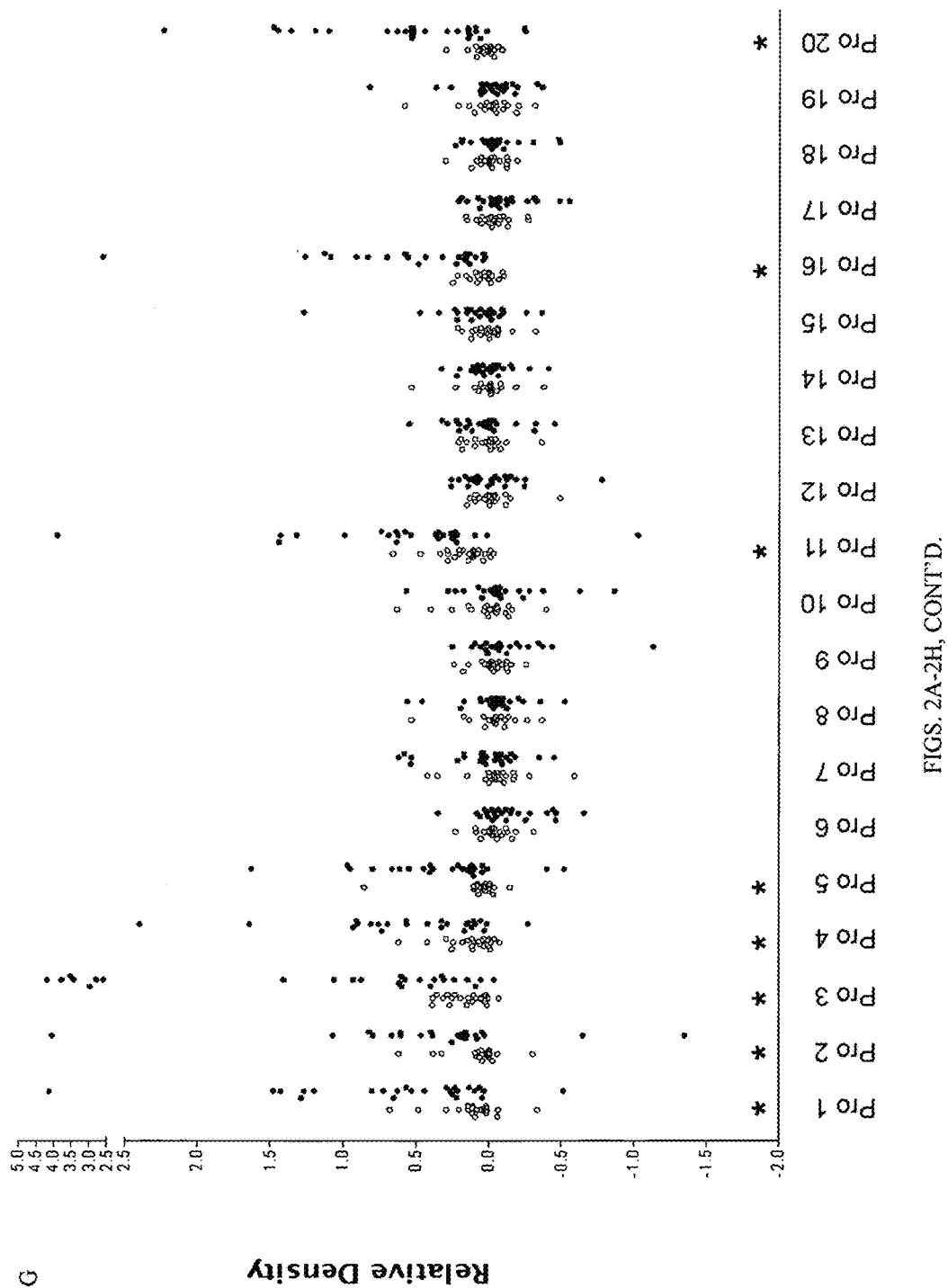
FIGS. 2A-2H, CONT'D.

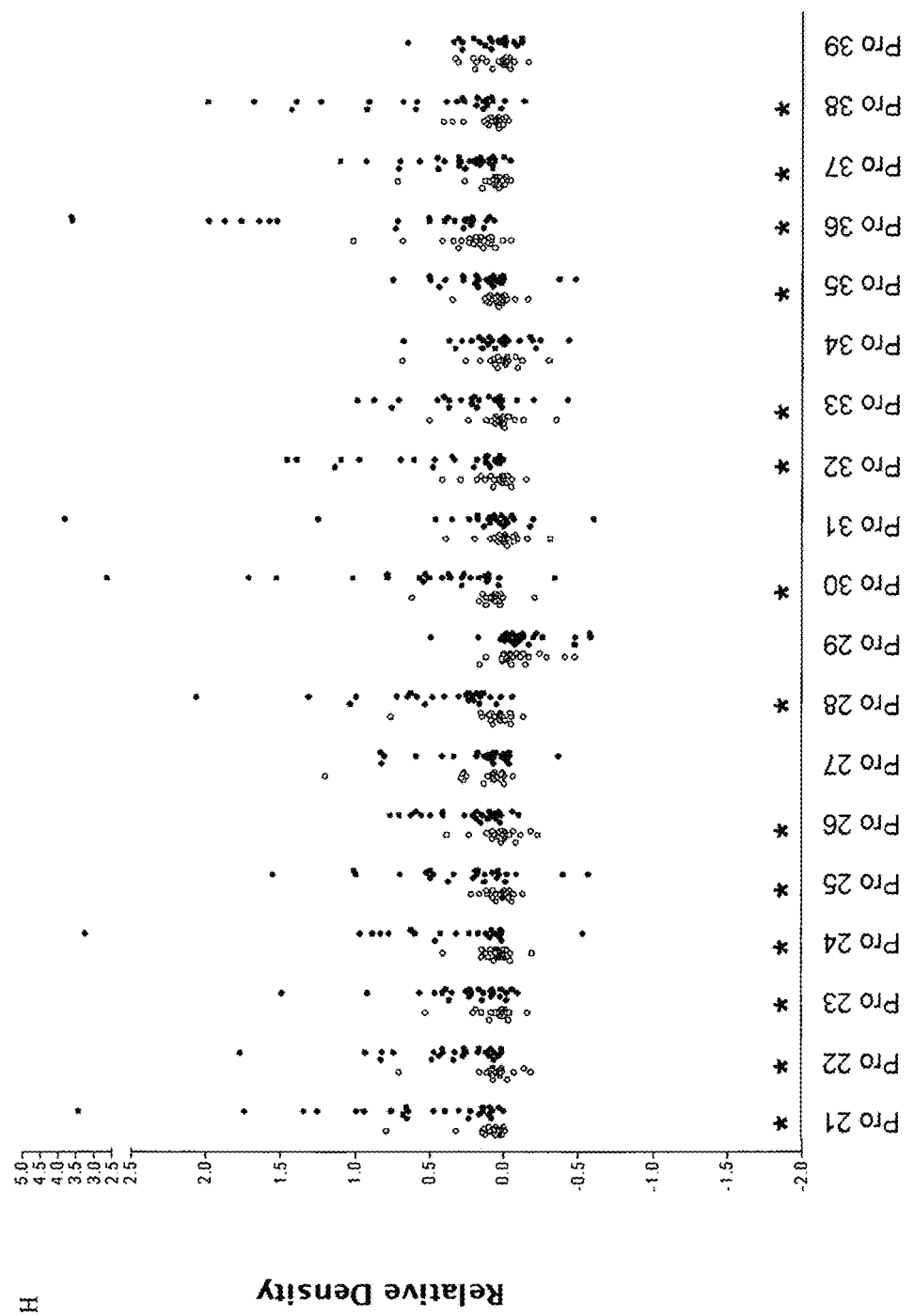
FIGS. 2A-2H, CONT'D.

FIGS. 3A-3F, CONT'D.

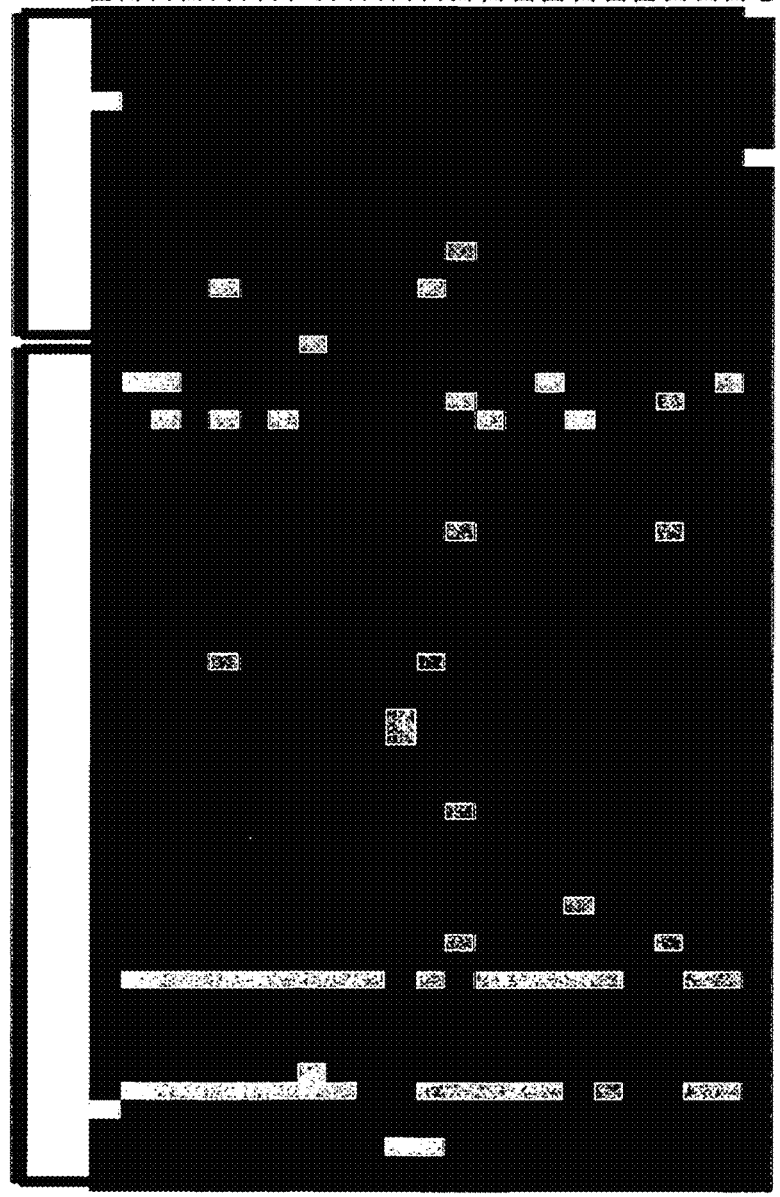
FIGS. 3A-3F, CONT'D.

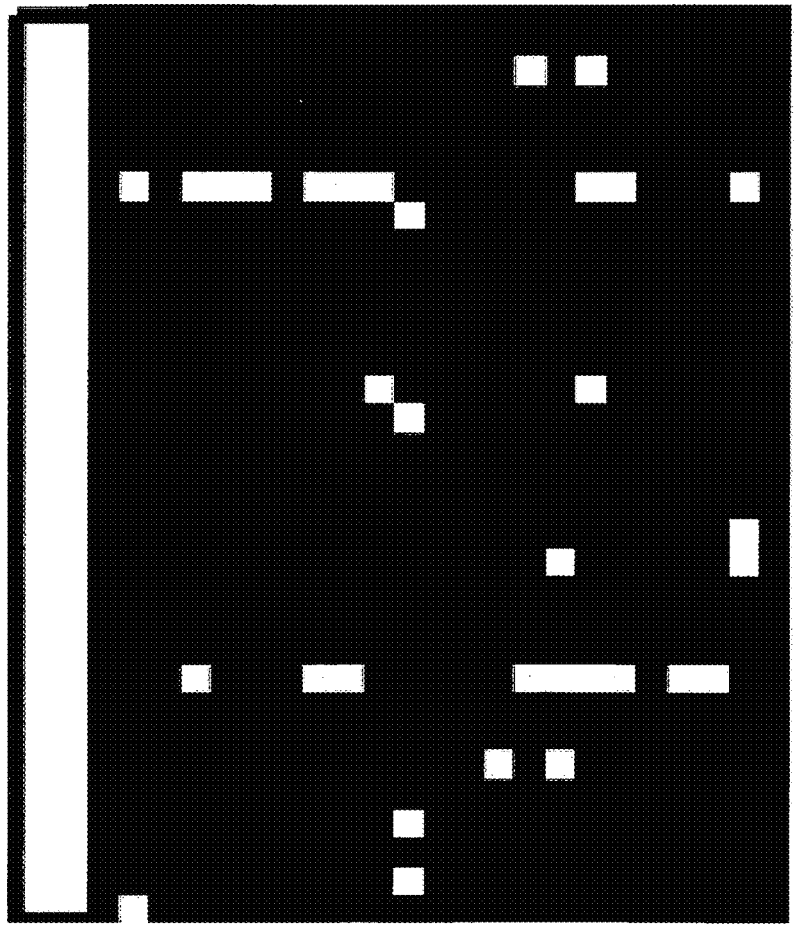
FIGS. 3A-3F, CONT'D.

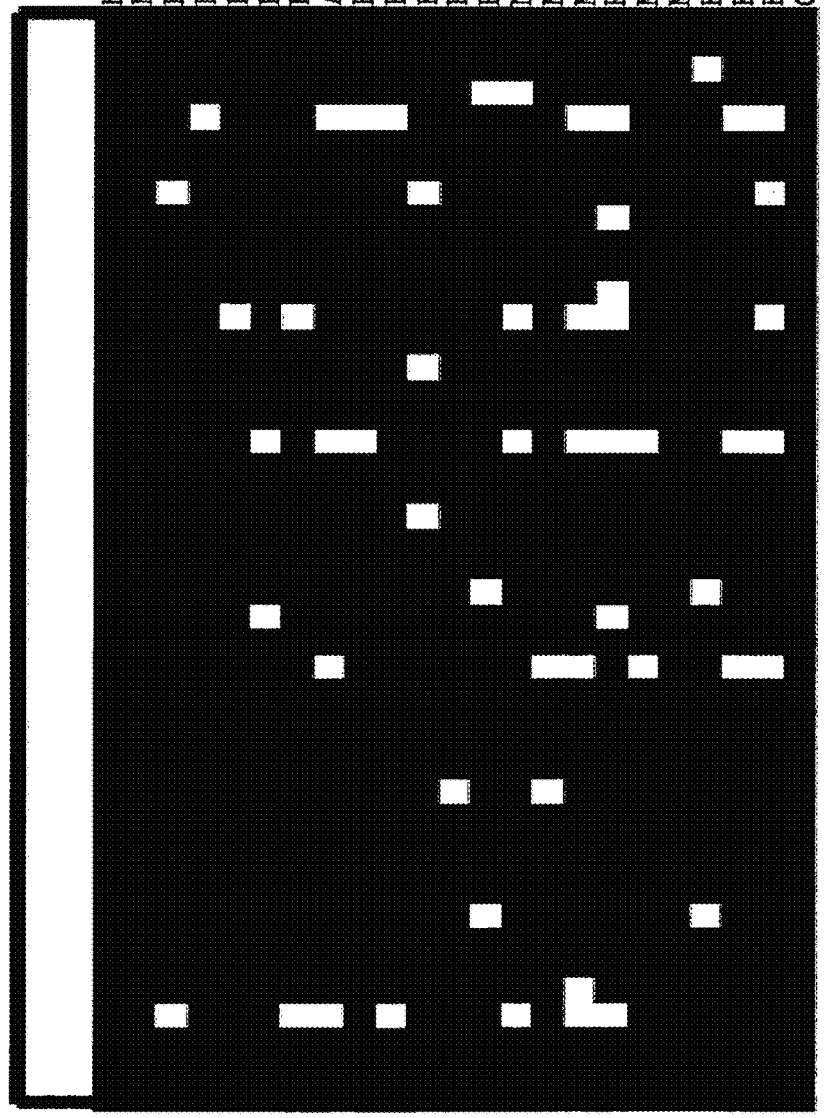
FIGS. 3A-3F, CONT'D.

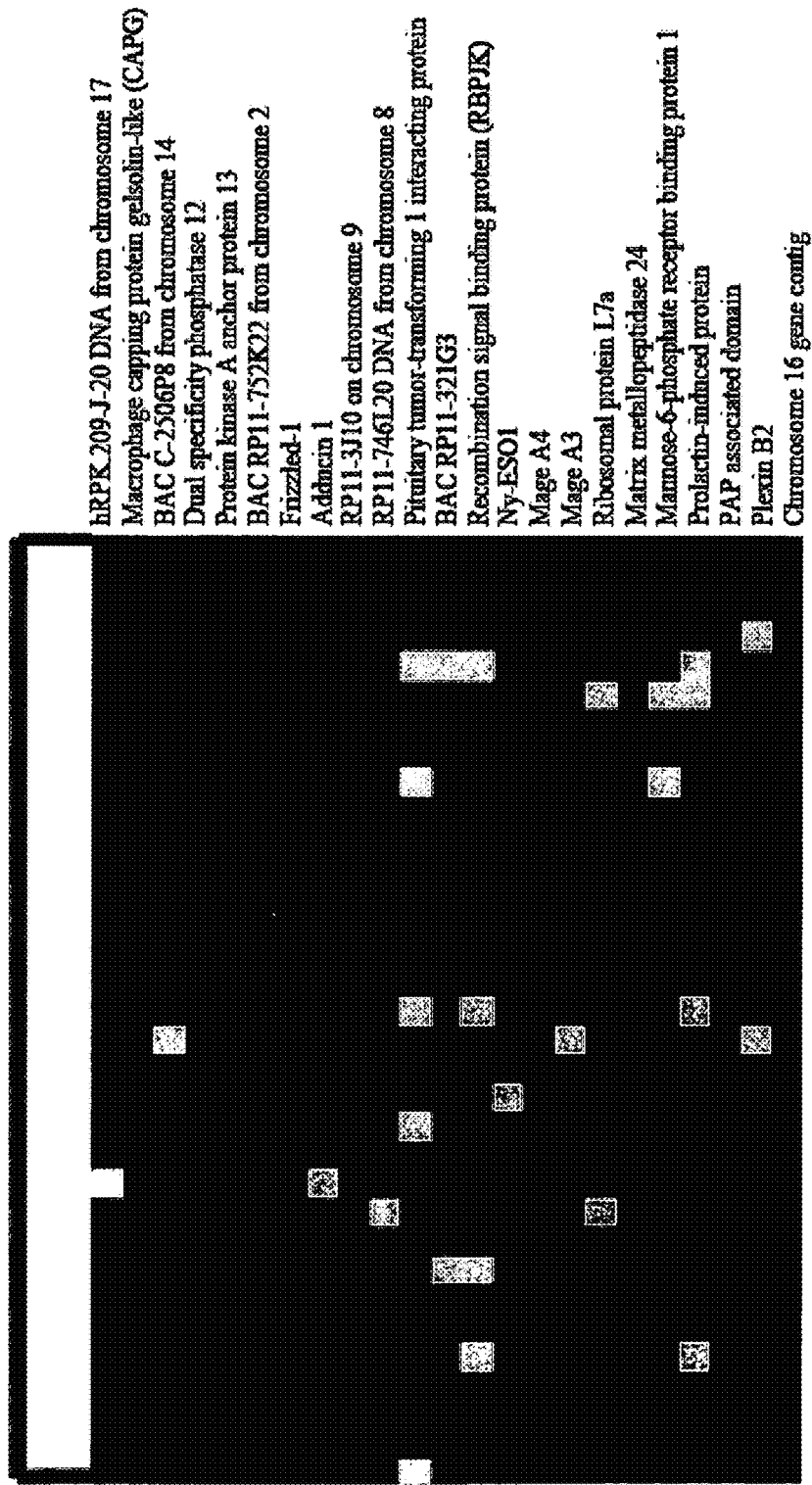
FIGS. 3A-3F, CONT'D.

DIAGNOSTIC EVALUATION OF ANTIBODY RESPONSES TO COMMONLY RECOGNIZED PROSTATE CANCER-ASSOCIATED ANTIGENS

CROSS-REFERENCE TO RELATED APPLICATION

This application is a continuation of U.S. application Ser. No. 13/088,594, filed Apr. 18, 2011, now abandoned, which claims the benefit of U.S. Provisional Patent Application No. 61/324,953, filed Apr. 16, 2010, each of which is incorporated herein by reference as if set forth in its entirety.

STATEMENT REGARDING FEDERALLY SPONSORED RESEARCH OR DEVELOPMENT

This invention was made with government support under RR016489 awarded by the National Institutes of Health. The government has certain rights in the invention.

SEQUENCE LISTING

A sequence listing is submitted in PDF and text formats on one Compact Disc-Read Only Memory (CD-ROM), in duplicate, and is incorporated herein by reference. "Copy 1" of the CD-ROM contains Seq List 960296_01933_ST25.PDF, created Dec. 23, 2015, 1620 KB and Seq List 960296_01933_ST25.TXT, created Dec. 23, 2015, 2695 KB. "Copy 2" of the CD-ROM contains Seq List 960296_01933_ST25.PDF, created Dec. 23, 2015, 1620 KB and Seq List 960296_01933_ST25.TXT, created Dec. 23, 2015, 2695 KB.

BACKGROUND

Prostate cancer is prevalent worldwide. Men living in the United States have approximately a 1 in 6 chance of being diagnosed with prostate cancer at some point during their lifetime, and approximately a 1 in 50 chance of dying from prostate cancer (Jemal et al., CA Cancer J. Clin. 59:225-249 (2009), incorporated herein by reference as if set forth in its entirety). The number of men afflicted with prostate cancer is increasing rapidly as the population of males over the age of 50 grows. Thus, strategies for detecting prostate cancer in its early stages are urgently needed.

Conventional prostate cancer screening methods, including digital rectal examination, transrectal ultrasound, and prostate specific antigen (PSA) testing, lack sensitivity and specificity. Elements of PSA screening are controversial: practitioners disagree on the best age for screening, how to interpret elevated PSA values, and how to identify prostate cancers in patients with low serum PSA values. There are also concerns that PSA screening may lead to unnecessary interventions that do not affect long-term outcome and survival (Greene et al., J Urol 182:2232-2241 (2009), incorporated herein by reference as if set forth in its entirety). To overcome the disadvantages of prostate cancer screening methods, researchers have attempted to identify antigens produced by tumor cells that can be utilized as prostate cancer markers. Serum-based screening methods have allowed for rapid identification of many tumor antigens in individuals with many different tumor types (Sahin et al., Proc. Nat. Acad. Sci. 92:11810-11813(1995), incorporated herein by reference as if set forth in its entirety). In fact, serum screening has been so successful that literally hundreds of cancer-associated antigenic proteins have been identified.

Serological identification of antigens by recombinant expression cloning (SEREX) has been used to prioritize potential vaccine targets for prostate cancer. Immunologically recognized proteins of the prostate have been identified by screening sera from: i) individuals with prostate cancer (Dunphy et al., Update Canc. Ther. 22:273-284 (2006); Fossa et al., Br. J. Cancer 83:743-749 (2000); Mooney et al., Int. J. Urol. 13:211-217 (2006)); ii) prostate cancer individuals treated with immune-active therapies (Dunphy et al., J. Immunother. 28:268-275 (2005)); and iii) prostate cancer individuals treated with standard androgen deprivation therapy (Morse and McNeel, Hum. Immunol. 71:496-504 (2010)); each of the foregoing references are herein incorporated by reference as if set forth in their entirety). Sera from individuals with prostate cancer were also used to directly screen a testis tissue cDNA expression library and a panel of defined cancer-testis antigens aberrantly expressed in solid tumors of different histologic types (Hoeppner et al., Cancer Immun. 6:1-7 (2006); Dubovsky and McNeel, Prostate 67:1781-1790 (2007), each incorporated herein by reference as if set forth in its entirety).

Chronic inflammation has been implicated in lung and colon cancers and might similarly promote the development of prostate cancers (Palapattu et al., Carcinogenesis 26:1170-1181 (2005); Narayanan et al., Prostate 69:133-141 (2009); McDowell et al., Prostate 70:377-389 (2010); Dennis et al., Urology 60:78-83 (2002); each incorporated herein by reference as if set forth in its entirety). Tumor-infiltrating lymphocytes are observed in prostate tumor specimens, and chronic inflammatory cells (e.g., lymphocytes and mononuclear cells) are observed adjacent to the earliest premalignant lesions of the prostate (De Marzo et al., Am. J. Pathol. 155:1985-1992 (1999) incorporated by reference herein as if set forth in its entirety). In rodents, chronic prostatitis appears to promote the development of prostate tumors (Gilardoni et al., J. Exp. Clin. Cancer Res. 18:493-504 (1999), incorporated by reference herein as if set forth in its entirety). Human prostate-infiltrating lymphocytes obtained at the time of surgery are oligoclonal suggesting that these lymphocytes recognize tissue-specific antigens (Mercader et al., Proc. Nat. Acad. Sci. 98:14565-14570 (2001); Sfanos et al., Prostate 69:1694-1703 (2009); each incorporated herein by reference as if set forth in its entirety).

While a number of antigens associated with prostate cancer have been identified, it has not yet been determined which of these antigens are predictive of a malignant or premalignant prostate. This is at least in part due to the variation in antibody-antigen profiles of individuals; not every antigen associated with prostate cancer or prostatitis is expressed in every affected individual and not every expressed antigen elicits an immune response in every affected individual. As such, no single antigen can serve as a reliable indicator of prostate cancer or prostatitis. The high level of variation of immunoresponsiveness among individuals has made it difficult to translate antigens associated with prostate cancer into tools useful for predicting prostate cancer, or predicting an increased risk of developing prostate cancer, in populations of men, wherein populations are defined as groups with or without a particular disease or disease stage. Screening men for all antigens that have been associated with prostate cancer is cost-prohibitive and impractical. Thus, there is a need in the art to identify a subset of antigens specific to antibodies associated with pre-malignant and malignant prostate tissue for identifying candidate individuals warranting further prostate examination.

BRIEF SUMMARY OF THE INVENTION

The present invention is broadly summarized as relating to a plurality of antigens that together form a set or panel of immunoreactive molecules suitable for identifying candidates for prostate cancer examination. Many cancer detection efforts rely on detecting, with varying degrees of specificity and sensitivity, cancer-associated antigens produced by tumor cells. In contrast, the present invention relies on detecting immunoresponses to tissue-associated antigens. The present invention contemplates using a plurality of these antigens to identify antibodies indicative of a pre-malignant or malignant prostate. As used herein, an "antigen" means a substance that when introduced into an animal stimulates the production of an antibody. An antigen can also be a substance produced by the body, wherein an immune response has been, or can be, elicited to that antigen. As used herein, an "antibody," is a specialized molecule that can specifically bind the antigen that triggered its production.

In a first aspect, the invention is summarized as an antigen panel for identifying immunoreactivity associated with a premalignant or malignant prostate, the panel comprising a plurality of antigens. As used herein, "immunoreactivity" refers to an animal's immune response to a particular antigen or antigens. One or more of the antigens may be previously known and identified as being recognized by antibodies in individuals having prostate cancer and/or prostatitis. In some embodiments of the first aspect, the panel elicits an immune response in at least about 33% of men with prostate cancer or prostatitis. In other embodiments of the first aspect, 9% of individuals with prostatitis or prostate cancer exhibit an immune response to at least three of the antigens in the panel. As use herein, "about" means within 5% of a stated range.

In some embodiments of the first aspect, the plurality of antigens in the antigen panel is selected from the group consisting of PRO1, PRO2, PRO3, PRO4, PRO5, PRO6, PRO7, PRO8, PRO9, PRO10, PRO11, PRO12, PRO13, PRO14, PRO15, PRO16, PRO17, PRO18, PRO19, PRO20, PRO21, PRO22, PRO23, PRO24, PRO25, PRO26, PRO27, PRO28, PRO29, PRO30, PRO31, PRO32, PRO33, PRO34, PRO35, PRO36, PRO37, PRO38, PRO39, PRO40, PRO41, CTA1, CTA2, CTA3, CTA4, CTA5, CTA6, CTA7, CTA5, CTA9, CTA10, CTA11, CTA12, CTA13, CTA14, CTA15, CTA16, CTA17, CTA18, CTA19, CTA20, CTA21, CTA22, CTA23, CTA24, CTA25, CTA26, CTA27, CTA28, CTA29, PCA1, PCA2, PCA3, PCA4, PCA5, PCA6, PCA7, PCA8, PCA9, PCA10, PCA11, PCA12, PCA13, PCA14, PCA15, PCA16, PCA17, PCA18, PCA19, PCA20, PCA21, PCA22, PCA23, PCA24, PCA25, PCA26, PCA27, PCA28, PCA29, PCA30, ADT1, ADT2, ADT3, ADT4, ADT5, ADT6, ADT7, ADT8, ADT9, ADT10, ADT11, ADT12, ADT13, ADT14, ADT15, ADT16, ADT17, ADT18, ADT19, ADT20, ADT21, ADT22, ADT23, ADT24, ADT25, ADT26, ADT27, and ADT28.

In another embodiment of the first aspect, the plurality of antigens in the panel includes ADT14, CTA3, CTA23, PCA6, PCA8, PCA10, PCA16, PRO5, PRO10, PRO12, PRO17, PRO18, PRO19, PRO20, PRO24, PRO25, PRO35, CTA27, PCA21, PRO40, PCA2, PRO34, and PRO32.

In a second aspect, the invention relates to a method for identifying human or non-human animals as candidates for prostate cancer examination. The method includes the steps of contacting an antigen panel as above with a sample containing at least one antibody specific to at least one antigen of the panel, and observing evidence of immunocomplex formation between at least one antibody from the sample and at least one antigen of the panel. As used herein, "immunocomplex" refers to a complex formed between an antibody and the antigen specifically recognized by the antibody. An individual is identified as a candidate if at least one immunocomplex forms between an antibody from the sample and an antigen in the panel. Samples appropriate for use in the method include, but are not limited to, tissues, cells, and bodily fluids, including blood.

In a third aspect, the present invention relates to a kit comprising an antibody detection panel. The kit comprises an antigen panel containing a plurality of antigens as disclosed herein optionally provided in a carrier or medium.

Unless otherwise defined, all technical and scientific terms used herein have the same meaning as commonly understood by one of ordinary skill in the art to which this invention belongs. Although suitable materials and methods for the practice or testing of the present invention are described below, other known materials and methods similar or equivalent to those described herein can be used.

Other objectives, advantages and features of the present invention will become apparent from the following specification taken in conjunction with the accompanying drawings.

BRIEF DESCRIPTION OF THE SEVERAL VIEWS OF THE DRAWINGS

FIG. 3A shows a heatmap analysis of the relative immunoreactivity for individual antigens indicated by spot color intensity (immunoreactive: white; intermediate: grey; not immunoreactive: black). FIGS. 3B-F illustrates a subset analysis for 23 antigens with the highest positive likelihood ratio values.

DETAILED DESCRIPTION OF PREFERRED EMBODIMENTS

Figure 1:
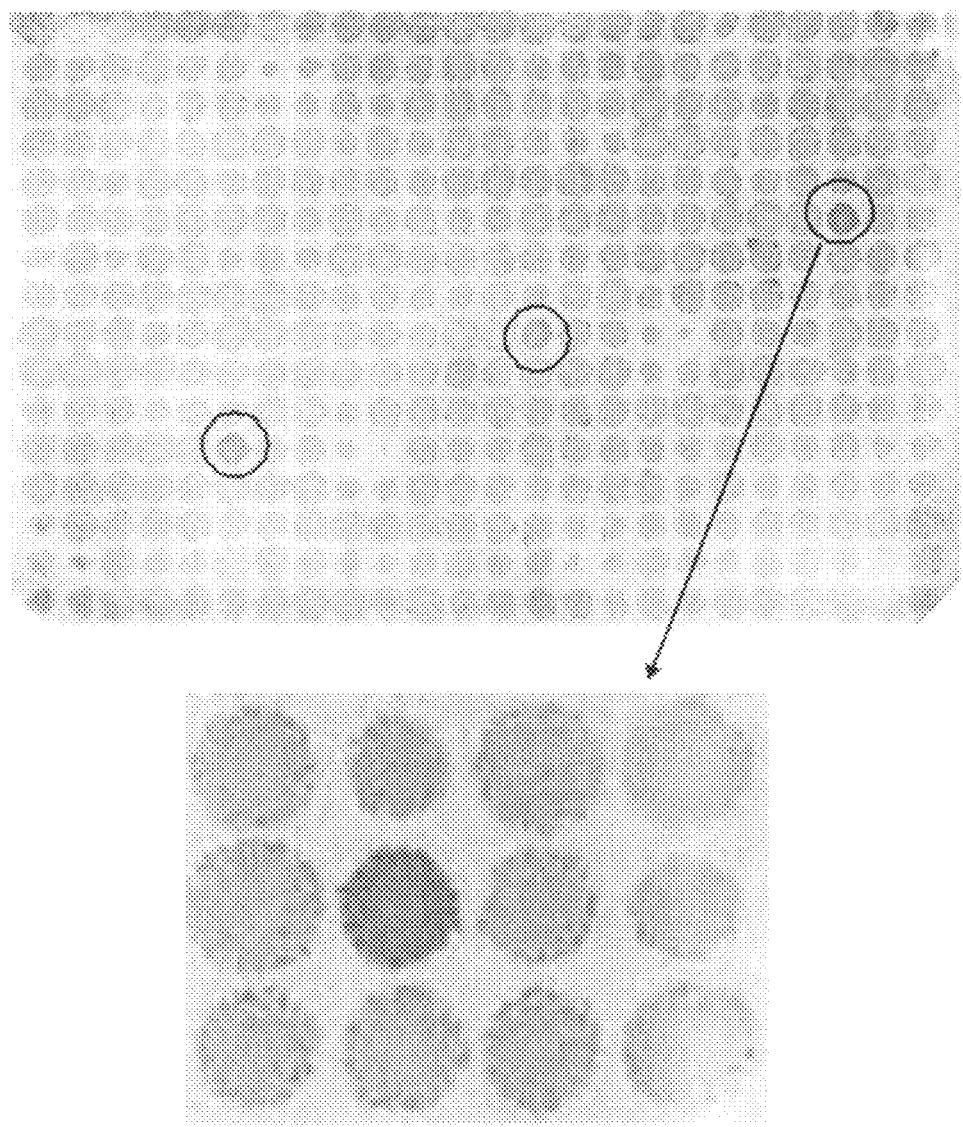
FIG. 1: illustrates high-throughput immunoblot analysis.
Figures 2A, 2B, 2C, 2D, 2E, 2F, 2G, 2H:
FIGS. 2A-2H: illustrate the mean relative density scores for healthy male control blood donors (n=25, open circles) and men with castrate-resistant prostate cancer (n=25, closed circles). Asterisks denote significantly higher median reactivity for the cancer population compared to the control population.

The present invention generally relates to a novel panel of a plurality of antigens for identifying immunoresponses associated with a premalignant or malignant prostate. As used herein, a "set" or a "panel" refers to a group of antigens associated with a premalignant or malignant prostate. As used herein, "immunoresponse" means the occurrence of a binding reaction between an antibody specific to an antigen and that antigen. As used herein, a premalignant prostate means a prostate characterized by tissue that is not yet malignant, but is poised to become malignant as evidenced by, for example, chronic inflammation or other conditions that can alter cell proliferation and/or cell death. Skilled artisans are familiar with conditions that are associated with changes in cell proliferation and conditions that are associated with changes in cell death. As used herein a malignant prostate refers to a prostate containing tumor-forming prostate epithelial cells.

In some embodiments, one or more of the antigens of the panel is associated with premalignant inflammation of the prostate. As used herein, "premalignant inflammation" means inflammation, the presence of which indicates an increase in an individual's risk for developing a malignant state or condition. Advantageously, the panel includes a plurality of antigens that make the panel more likely to detect immunoreactivity when exposed to antibody-containing samples compared to using a single antigen alone. In some preferred embodiments, antigens having higher specificity for prostate cancer are included in the panel, wherein relative specificity is based on receiver operating curve analysis. In other preferred embodiments, antigens with a positive likelihood ratio greater than 4 (sensitivity/(1−specificity)) are included in the panel. Sensitivity and specificity are based on immunoreactivity of a population of subjects with prostate disease relative to a control population. As used herein, "sensitivity" of an antigen refers to the proportion of positive subjects (i.e., subjects with prostate cancer or prostatitis) identified as positive by presence of an immunoresponse to a particular antigen in an assay. As used herein, "specificity" of an antigen refers to the proportion of negative subjects (i.e., control subjects without prostate cancer or prostatitis) identified as negative by absence of an immunoresponse to a particular antigen in an assay. The likelihood ratio used to rank antigens is a statistical model used to express how many times more likely a dataset is to fit one statistical model rather than another. For example, an antigen having a likelihood ratio of 4 is 4 times more likely to elicit an immunoresponse in a subject having prostatitis or prostate cancer relative to a patient lacking prostatitis or prostate cancer. An antigen can be a natural or synthetic protein or fragment thereof, polysaccharide, or nucleic acid. Skilled artisans know that antigens can induce an immune response and elicit antibody formation. Antibodies can be molecules synthesized in response to the presence of a foreign substance, wherein each antibody has specific affinity for the foreign material that stimulated its synthesis. The specific affinity of an antibody need not be for the entire molecular antigen, but for a particular site on it called the epitope (Kindt et al., Kuby Immunology, 6th Edition 574 pps, (2006), incorporated herein by reference as if set forth in its entirety). Antibodies can be, for example, a natural or synthetic protein or fragment thereof, or nucleic acids (e.g., aptamers) with protein-binding or other antigen-binding characteristics. Antibodies can be produced in response to antigenic stimuli including, but not limited to, exposure to foreign proteins, microorganisms, and toxins. When the panel is contacted with a sample containing at least one antibody specific to an antigen in the panel, an immunocomplex forms between the antigen and the antibody specific for the antigen. One of ordinary skill in the art can assess antigen-antibody imunocomplex formation by techniques commonly used in the art. Examples of suitable techniques to assess immunocomplex formation include phage immunoblot, ELISA, and radioimmunoassay. See, e.g., (Dubovsky et al., J. Immunother. 30:675-683 (2007), incorporated herein by reference as if set forth in its entirety). Samples suitable for use with the method include tissues, cells, and bodily fluids. Preferably, the sample is serum.

In a preferred embodiment, at least about 38% of individuals who have prostate cancer and at least about 33% of individuals who have prostatitis are immunoreactive to at least one antigen of the panel. In another preferred embodiment, at least about 10% of individuals who have prostate cancer and at least about 9% of individuals who have prostatitis are immunoreactive to at least three antigens of the panel. In still another preferred embodiment, antigens of the panel are selected based on their capacity in aggregate to elicit an immune response in at least about 33% of individuals with prostatitis or prostate cancer.

Prostate cancer-relevant cancer-testis antigens (CTA) normally expressed only in MHC class I-deficient germ cells but aberrantly expressed in solid tumors of various histologic types, are suitable for use in the panel. Suitable CTA antigens include, but are not limited to, CTA1, CTA2, CTA3, CTA4, CTA5, CTA6, CTA7, CTA5, CTA9, CTA10, CTA11, CTA12, CTA13, CTA14, CTA15, CTA16, CTA17, CTA18, CTA19, CTA20, CTA21, CTA22, CTA23, CTA24, CTA25, CTA26, CTA27, CTA28, and CTA29. Antigens identified in prostate cancer individuals treated with androgen deprivation therapy (ADT) are also suitable for use in this panel. Suitable ADT antigens include, but are not limited to, ADT1, ADT2, ADT3, ADT4, ADT5, ADT6, ADT7, ADT8, ADT9, ADT10, ADT11, ADT12, ADT13, ADT14, ADT15, ADT16, ADT17, ADT18, ADT19, ADT20, ADT21, ADT22, ADT23, ADT24, ADT25, ADT26, ADT27, and ADT28. Antigens identified in prostate cancer individuals treated with non-ADT prostate cancer therapies (PCA) are also suitable for use in this panel. Suitable PCA antigens include but are not limited to, PCA1, PCA2, PCA3, PCA4, PCA5, PCA6, PCA7, PCA8, PCA9, PCA10, PCA11, PCA12, PCA13, PCA14, PCA15, PCA16, PCA17, PCA18, PCA19, PCA20, PCA21, PCA22, PCA23, PCA24, PCA25, PCA26, PCA27, PCA28, PCA29, and PCA30. Alternatively, antigens identified in subjects with chronic prostatitis (PRO) are suitable for use in this panel. Suitable PRO antigens include, but are not limited to, PRO1, PRO2, PRO3, PRO4, PRO5, PRO6, PRO7, PRO5, PRO9, PRO10, PROM PRO12, PRO13, PRO14, PRO15, PRO16, PRO17, PRO18, PRO19, PRO20, PRO21, PRO22, PRO23, PRO24, PRO25, PRO26, PRO27, PRO28, PRO29, PRO30, PRO31, PRO32, PRO33, PRO34, PRO35, PRO36, PRO37, PRO38, PRO39, PRO40, and PRO41. Exemplary conditions for preparing antigens having epitopes specifically recognized by antibodies specific to the epitopes, are well-known by those of ordinary skill in the art.

In a preferred embodiment, the panel includes ADT14, CTA3, CTA23, PCA6, PCA8, PCA10, PCA16, PRO5, PRO10, PRO12, PRO17, PRO18, PRO19, PRO20, PRO24, PRO25, PRO35, CTA27, PCA21, PRO40, PCA2, PRO34, and PRO32. Omitting one or more of these antigens from the panel might affect the panel's sensitivity. Similarly, adding one or more antigen to this panel might affect the panel's sensitivity. However, a skilled artisan understands that increasing or decreasing the number of antigens in this preferred panel might still provide an acceptable panel of antigens for identifying candidates for further prostate cancer examination.

In another preferred embodiment, the panel includes antigens that have a high likelihood of eliciting immunoresponses in subjects who are candidates for further prostate cancer examination, relative to subjects who are not candidates for further prostate examination, as measured by positive likelihood ratio. In some of these preferred embodiments, antigens of the panel have a positive likelihood ratio of at least 4 (sensitivity/(1−specificity)).

In another embodiment, the present invention provides a method for identifying individuals as candidates for further prostate cancer examination. In the method, a panel is contacted with a sample containing one or more antibodies under conditions suitable for antigen-antibody immunocomplex formation. The skilled artisan knows exemplary conditions to allow high-affinity antigen-antibody binding (e.g., Dubrovsky et al., 2007 supra). In the method, presence of an immunocomplex indicates that the individual from whom the sample was obtained is a candidate for further prostate cancer examination.

The disclosed methods can be performed in a single or multi-well format in which each one of the plurality of antigens is placed in a separate well of a multi-well assay plate or, alternatively, in a single container format in which the entire panel of antigens is placed in a single well. The method may be performed in a qualitative format to detect the presence or absence of immunocomplexes, or in a quantitative format to provide a quantitative measurement of the antibodies in a sample. Exemplary conditions used to assay antigens of the inventive panel are well-known by those of ordinary skill in the art.

In another embodiment, the antigen panel can be provided as part of a kit containing a carrier or medium suitable for antigen storage.

The invention will be more fully understood upon consideration of the following non-limiting Examples.

EXAMPLES

Example 1: Diagnostic Evaluation of Antibody Responses to Prostate Cancer-Associated Antigens Multiple antigens were evaluated to identify a subset of immunoreactive antigens in humans with prostate disease. IgG responses were evaluated in subjects with prostate cancer, chronic prostatitis, and in men without prostate disease using phage immunoblot methodology. Results indicated that subjects with prostate cancer or prostatitis have antibodies specific for multiple common antigens: of 128 proteins tested, a subset containing 23 proteins was identified to which antibodies were detected in 38% of subjects with prostate cancer and 33% subjects with prostatitis versus 6% of controls. These results suggest an association between inflammatory conditions of the prostate and prostate cancer, and suggest that antibody responses to a panel of commonly-recognized prostate antigens can be used to identify subjects at risk for prostate cancer.

Materials and Methods

High Throughput Immunoblot (HTI):

Phage immunoblot analysis was performed essentially as described by Dubovsky et al., J Immunother 30:675-683 (2007), incorporated by reference herein as if set forth in its entirety. Briefly, panels of 128 lambda phage encoding unique prostate-associated antigens were assembled (Table I). Phage included those antigens initially identified in individuals with prostate cancer or chronic prostatitis by SEREX (Dunphy et al., 2004 supra; Dunphy et al., 2005, supra; Morse and McNeel, 2010 supra; Hoeppner et al., 2006 supra), or were constructed to express specific genes of interest based on prior studies (Dubovsky et al., 2007 supra; Olson and McNeel, Prostate 67:1729-1739 (2007) incorporated herein by reference as if set forth in its entirety). The following antigens were included in the panel: 29 cancer-testis antigens (CTA), 41 antigens identified in individuals with chronic prostatitis (PRO), 28 antigens identified in individuals treated with androgen deprivation (ADT), and 30 antigens identified in individuals treated with other therapies (PCA).

100,000 pfu lambda phage each carrying a gene that encodes one of the 128 antigens of the panel were robotically spotted in triplicate in a 16×24 array onto lawns of $E.$ $coli$ (XL-1 blue strain) growing in agar-containing Omni-Tray plates. Replicates for individual antigens were staggered in position across the array to account for regional variation on individual filters. For initial studies, phage encoding human immunoglobulin G (IgG) were included as a positive control and empty phage constructs were similarly included as a negative control. Plates were allowed to dry at room temperature for 20 minutes and incubated at 37° C. for 4 hours after which nitrocellulose membranes suffused with 10-mM isopropyl β-D-thiogalactopyranoside (IPTG) (Fisher Scientific, Pittsburgh, Pa.) were overlaid. Plates were incubated at 37° C. overnight to allow for recombinant expression of the antigen encoded by the protein. After 16-20 hours, membranes were removed, washed twice in TBST (50 mM Tris pH 7.2, 100 mM NaCl, 0.5% Tween-20) for 10 minutes and once in TBS (50 mM Tris pH 7.2, 100 mM NaCl) for an additional 10 minutes. Membranes were blocked in blocking solution (TBST+1% BSA), and incubated at 4° C. with human sera (diluted 1:100 in blocking solution) overnight. Membranes were washed the following day and blocked prior to incubation with a mouse anti-human IgG antibody conjugated to alkaline phosphatase (Sigma, St. Louis, Mo.) to detect human IgG. Membranes were washed again and incubated in 0.3 mg/mL nitro blue tetrazolium chloride (NBT) (Fisher Scientific) and 0.15 mg/mL 5-bromo 4-chloro 3-indoylphosphate (BCIP) (Fisher Scientific) in 100-mM Tris 9.5, 100-mM NaCl, and 5-mM $MgCl_2$ to detect immunoreactivity. Membranes were washed with large volumes of deionized water and dried at room temperature prior to evaluation.

Membranes were scanned using a color image scanner and the digital format aligned with a 16×24 grid using densitometry software (ImageQuant TL, Amersham Biosciences, GE Healthcare Life Sciences, Piscataway, N.J.). For initial studies, immunoreactivity was quantified by measuring the density at each spot; values of replicates for individual antigens were averaged. Background correction was then made by subtracting the average of empty phage construct replicate densities on individual membrane and normalized by dividing by the average of IgG positive control replicate densities on each membrane. Transformation of densitometry data resulted in density values for individual antigens relative to a negative control and a positive control (set at 0.0 and 1.0 respectively). For subsequent studies, immunoreactivity was judged as "positive" or "negative" by visual inspection, as previously described (Dunphy et al., J. Clin. Immunol. 24:492-501 (2004), incorporated herein by reference as if set forth in its entirety; Dubovsky et al., 2007 supra). Briefly, four independent individuals looked at each membrane and scored individual spots as immunoreactive or not reactive by visually comparing each spot to a negative control. Antigens for which 0-1 of replicates determined immunoreactive with individual sera were defined as negative for immunoreactivity, and for which 2-3 of the replicates determined immunoreactive were defined as positive.

TABLE I

One embodiment of the antigen panel.

| Designation | GenBank Accession | SEQ ID NO: | Gene name |
|---|---|---|---|
| PRO1 | NM_006423.1 | 1 | Rab acceptor |
| PRO2 | NM_007124.1 | 2 | U-trophon |
| PRO3 | NM_000484.1 | 3 | Amyloid Beta (4) precursor protein |
| PRO4 | NM_002709.1 | 4 | Protein Phosphatase 1 |
| PRO5 | AC005822.1 | 5 | hRPK.209-J-20 DNA from chromosome 17 |
| PRO6 | AF308301.1/ NM_030811.2 | 6 | NY-BR-87/Ribosomal protein S26 |
| PRO7 | NM_014761.1 | 7 | KIAA0174 from chromosome 16 |
| PRO8 | AF273042.1 | 8 | Cutaneous T cell lymphoma tumor antigen sel-1 |
| PRO9 | AK096728.1 | 9 | FLJ39409 Cdna |
| PRO10 | NM_001747.1 | 10 | Macrophage capping protein gelsolin-like (CAPG) |
| PRO11 | NM_000717.2 | 11 | Carbonic anhydrase IV |
| PRO12 | AL136040.5 | 12 | BAC C-2506P8 from chromosome 14 |
| PRO13 | AC084864.4 | 13 | RP11-738B7 DNA from chromosome 7 |
| PRO14 | NM_001813.1 | 14 | Centromere protein E |
| PRO15 | M27274.1 | 15 | Prostate specific antigen (PSA) |
| PRO16 | NM_012116.2 | 16 | Cas-Br-M ecotropic retroviral transforming sequence c (CBLC) |
| PRO17 | BC006286.1 | 17 | Dual specificity phosphatase 12 |
| PRO18 | NM_144767.1/ BC017368.1/ AF126008.1 | 18 | Protein kinase A anchor protein 13/ lymphoid blast crisis oncogene/ breast cancer nuclear receptor-binding auxiliary protein (BRX) |
| PRO19 | AC073879.7 | 19 | BAC RP11-752K22 from chromosome 2 |
| PRO20 | AB017363.1 | 20 | Frizzled-1 |
| PRO21 | AL365273.25 | 21 | RP11-429G19 DNA from chromosome 10 |
| PRO22 | XM_047011.2 | 22 | o-fucosyltansferase |
| PRO23 | NM_017582.3 | 23 | NICE5 |
| PRO24 | NM_014190.1 | 24 | Adducin 1 |
| PRO25 | AL138752.5 | 25 | RP11-3J10 on chromosome 9 |
| PRO26 | BC024007.1 | 26 | Chitobiase |
| PRO27 | AK001572.1 | 27 | FLJ10710 cDNA |
| PRO28 | AL356915.19 | 28 | RP11-3J10 on chromosome 13 |
| PRO29 | NM_006117.1/ AF257175.1 | 29 | Peroxisomal D3, D2 enoyl CoA isomerase/Hepatocellular carcinoma associated antigen 64 |
| PRO30 | XM_033511.8 | 30 | Helicase with SNF2 domain |
| PRO31 | AF039689.1/ XM_083939.1/ AF432221.1 | 31 | NY-CO-7/STUB1/CLL-associated antigen KW-8 |
| PRO32 | AC021558.10 | 32 | RP11-746L20 DNA from chromosome 8 |
| PRO33 | NM_031946.2 | 33 | Centaurin gamma 3 |
| PRO34 | BC034250.1 | 34 | Pituitary tumor-transforming 1 interacting protein |
| PRO35 | AC069506.14 | 35 | BAC RP11-321G3 |
| PRO36 | AC011489.6 | 36 | CTB-179K24 DNA on chromosome 19 |
| PRO37 | NM_032415.2 | 37 | Caspase domain recruitment (CARD11) |
| PRO38 | NM_003379.3 | 38 | Cytovillin 2 |
| PRO39 | BC029529.1 | 39 | Beta tubulin |
| PRO40 | L07872.1 | 40 | Recombination signal binding protein (RBPJK) |
| PRO41 | NM_006455.1 | 41 | Nucleolar autoantigen/MAD-Pro-34 |
| CTA1 | NM_004988 | 42 | Mage A1 |
| CTA2 | BC007343 | 43 | SSX-2 |
| CTA3 | AJ003149 | 44 | Ny-ESO1 |
| CTA4 | NM_021123 | 45 | Gage 7 |
| CTA5 | U90841 | 46 | SSX-4 |
| CTA6 | BC015020 | 47 | NXF-2 |
| CTA7 | BC022011 | 48 | TPX 1 |
| CTA8 | BC009538 | 49 | Xage 1 |
| CTA9 | BC002833 | 50 | Lage 1 |
| CTA10 | BC010897 | 51 | Page 1 |
| CTA11 | BC081566 | 52 | Mage E1 |
| CTA12 | BC054023 | 53 | Span XC |
| CTA13 | BC064547 | 54 | Adam 2 |
| CTA14 | BC037775 | 55 | TSP 50 |
| CTA15 | BC034320 | 56 | NY-SAR 35 |
| CTA16 | BC022064 | 57 | Fate 1 |
| CTA17 | BC009230 | 58 | Page 5 |
| CTA18 | BC023635 | 59 | Lip1 |
| CTA19 | BC032457 | 60 | SPA17 |
| CTA20 | BE387798 | 61 | Mage A8 |
| CTA21 | BE897525 | 62 | Mage B1 |
| CTA22 | BC026071 | 63 | Mage B2 |
| CTA23 | BC017723 | 64 | Mage A4 |
| CTA24 | BC001003 | 65 | SSX-1 |
| CTA25 | BC069397 | 66 | Gage 2 |
| CTA26 | BC069470 | 67 | Gage 4 |
| CTA27 | BC016803 | 68 | Mage A3 |
| CTA28 | NM_002762 | 69 | MAD-CT-1 |
| CTA29 | AK097414 | 70 | MAD-CT-2 |
| PCA1 | NM_025161.4 | 71 | Chromosome 17 gene contig. |
| PCA2 | NM_000972.2 | 72 | Ribosomal protein L7a |
| PCA3 | NM_152636.2 | 73 | Chromosome 12 gene contig. |
| PCA4 | NM_001134194.1 | 74 | Prostatic acid phosphatase |
| PCA5 | NM_003291.2 | 75 | Tripeptidyl peptidase II |
| PCA6 | NM_006690.3 | 76 | Matrix metallopeptidase 24 |
| PCA7 | NM_000990.4 | 77 | Ribosomal protein L27a |
| PCA8 | NM_002652.2 | 78 | Prolactin-induced protein |
| PCA9 | NM_005349.2 | 79 | Immunoglobulin Kappa J region |
| PCA10 | NM_005817.2 | 80 | Mannose-6-phosphate receptor binding protein 1 |
| PCA11 | NM_013267.2 | 81 | Glutaminase 2 |
| PCA12 | NM_018979.2 | 82 | WNK lysine deficient protein kinase 1 |
| PCA13 | NM_020718.3 | 83 | Ubiquitin specific peptidase 31 |
| PCA14 | NM_003007.2 | 84 | Semenogelin I, transcript variant 1 |
| PCA15 | NM_022735.3 | 85 | Acyl-coenzyme A binding domain containing 3 |
| PCA16 | NM_001040284.1 | 86 | PAP associated domain |
| PCA17 | NM_020187.2 | 87 | Chromosome 3 gene contig. |
| PCA18 | NM_002712.1 | 88 | Protein phosphatase 3, regulatory subunit 7 |
| PCA19 | NM_014220.2 | 89 | Transmembrane 4 L6 family member 1 |
| PCA20 | NM_001135592.1 | 90 | Ribosomal protein S27a |
| PCA21 | NM_012401.2 | 91 | Plexin B2 |
| PCA22 | NM_000985.3 | 92 | Ribosomal protein L17 |
| PCA23 | NM_080608.3 | 93 | Chromosome 20 gene contig. |
| PCA24 | NM_005165.2 | 94 | Aldolase C |
| PCA25 | NM_000969.3 | 95 | Ribosomal protein L5 |
| PCA26 | NM_001958.2 | 96 | Eukaryotic translation elongation factor 1 alpha 1 |
| PCA27 | NM_025108.2 | 97 | Chromosome 16 gene contig. |
| PCA28 | NM_015358.2 | 98 | Zinc-finger protein, CW type with coiled-coil domain 3 |
| PCA29 | NM_001130410.1 | 99 | Acetyl-coenzyme A acyltransferase 1 |
| PCA30 | NM_000044.2 | 100 | Androgen receptor ligand-binding domain |
| ADT1 | NM_004759.3 | 101 | Mitogen-activated protein kinase-activated protein kinase 2 |
| ADT2 | NM_001103.2 | 102 | Actinin alpha 2 |
| ADT3 | NM_002518.3 | 103 | Neuronal PAS domain protein 2 (NPAS2) |
| ADT4 | NM_033138.2 | 104 | Caldesmon 1 (CALD1) |
| ADT5 | NM_001459.2 | 105 | fms-related tyrosine kinase 3 ligand |
| ADT6 | NM_022474.2 | 106 | Membrane protein, palmitoylated 5 (MAGUK p55 subfamily member 5) |
| ADT7 | NM_006022.2 | 107 | TSC22 domain family, member 1 (TSC22D1) |
| ADT8 | NM_001001522.1 | 108 | Transgelin |
| ADT9 | NM_022758.4 | 109 | Chromosome 6 gene contig |
| ADT10 | NM_002695.3 | 110 | polymerase (RNA) II (DNA directed) polypeptide E (POLR2E) |

TABLE I-continued

One embodiment of the antigen panel.

| Designation | GenBank Accession | SEQ ID NO: | Gene name |
|---|---|---|---|
| ADT11 | NM_001018160.1 | 111 | NEDD8 activating enzyme subunit 1 (NAE1) |
| ADT12 | NM_015313.1 | 112 | Rho guanine nucleotide exchange factor 12 (ARHGEF12) |
| ADT13 | NM_152374.1 | 113 | Chromosome 1 gene contig |
| ADT14 | NM_001100873.1 | 114 | Chromosome 16 gene contig |
| ADT15 | NM_001136204.1 | 115 | Regulator of chromosome condensation 2 (RCC2) |
| ADT16 | NT_006713.15 | 116 | Chromosome 5 gene contig (splicing factor, arginine/serine-rich 12) |
| ADT17 | NM_025157.3 | 117 | Paxillin (PXN) |
| ADT18 | NM_016143.2 | 118 | NSFL1 (p97) cofactor (p47) NSFL1C |
| ADT19 | NM_004913.2 | 119 | Chromosome 16 gene contig |
| ADT20 | NM_207356.2 | 120 | Chromosome 1 gene contig |
| ADT21 | NM_003104.4 | 121 | Sorbitol dehydrogenase (SORD) |
| ADT22 | NT_006316.16 | 122 | Chromosome 4 gene contig (solute carrier family 2, facilitated glucose transporter) |
| ADT23 | NM_013336.3 | 123 | Sec 61 alpha 1 subunit |
| ADT24 | NM_002474.2 | 124 | Myosin heavy chain 11 (MYH11) |
| ADT25 | NR_002819.2 | 125 | Metastasis associated lung adenocarcinoma transcript 1 (MALAT1) |
| ADT26 | NM_001012321.1 | 126 | Similar to lamanin receptor 1 (ribosomal protein SA (RPSA), from chromosome 19) |
| ADT27 | NT_009952.14 | 127 | Chromosome 13 gene contig (heparan-sulfate 6-O-sulfotransferase 3) |
| ADT28 | NM_021239.2 | 128 | RNA binding motif protein 25 (RBM 25) |

Statistical Analyses:

Data collected from preliminary studies analyzing individuals with castrate-resistant prostate cancer and normal male blood donors were plotted as relative density values representing detection of antibodies specific to 125 prostate cancer-associated antigens for individual individuals. Median relative density values for individual antigens were calculated in both castrate-resistant prostate cancer samples and normal control samples and the non-parametric Wilcoxon Rank Sum test was used to compare the medians of the two groups. The Benjamini-Hochberg False-Discovery Rate (FDR) method for multiple testing was used to control the type I error (Benjamini et al., J. Roy. Stat. Soc. B (Method) 57:289-300 (1995) incorporated by reference herein as if set forth in its entirety). The frequencies of IgG responses were compared between populations using Fisher's exact test. Receiver Operating Curve (ROC) analysis was performed to identify a subset of prostate cancer-associated antigens with the highest predictive value for detecting prostate cancer cases when compared to normal controls. The positive likelihood ratio value was used to quantify the predictive value for individual markers. The proportions of individuals with at least one positive IgG response and the proportions of individuals with at least three positive IgG responses in the subset of predictive markers were compared between populations by performing logistic regression analysis where population groups were included as factors. Dunnett's multiple testing procedure was used to compare the proportions between the individual populations and the control (normal) group. All p-values are two-sided, with $p<0.05$ indicating statistically significant differences. The data analysis was performed using SAS® version 9.2 software (SAS Corp., Cary, N.C.).

Individual Populations:

Sera were obtained from individuals with chronic prostatitis (n=45, median age 42, age range 19-62), prostate cancer (n=151, median age 67, age range 44-86), and men without a history of known prostate disease (n=78, median age 32, age range 18-62). Among the individuals with prostate cancer, 18 were collected from individuals at the time of diagnosis prior to definitive radiation treatment or prostatectomy (pretreatment), 32 were collected from individuals after definitive treatment without evidence of disease recurrence (limited stage), 44 were collected from individuals with metastatic disease recurrence on androgen deprivation therapy (androgen-dependent), and 57 were collected from individuals with castrate-resistant, metastatic disease. Sera were also obtained from male individuals with other cancers (melanoma, n=4; renal, n=17; testicular, n=5; other, n=5; median age 58, age range 30-74) for use as controls. All subjects gave written Institutional Review Board-approved consent for the use of their blood for immunological studies. Blood was collected at the University of Wisconsin-Madison Hospital and Clinics (Madison, Wis.) or at the University of Washington Medical Center (Seattle, Wash.), and sera were stored in aliquots at −20° C. to −80° C. until used for analysis.

Results

Individuals with Prostate Cancer have Higher Frequencies of Detectable Antibodies Specific for Prostate Cancer-Associated Antigens than Men without Cancer.

To determine if specific antigens are commonly recognized in the sera of individuals with prostate cancer, and if a particular set of antigens is more frequently recognized than other antigen sets, phage encoding 125 unique, prostate cancer-associated antigens obtained from prior studies (Table I) were spotted in replicate onto bacterial lawns, transferred to nitrocellulose membranes, and probed with individual sera samples, as illustrated in FIG. 1. IgG specific for phage-encoded plaques were detected using a mouse anti-human IgG antibody, immunoreactivity was quantified by densitometry, and then normalized to internal controls (0=reactivity equivalent to phage not encoding a protein; 1=reactivity equivalent to phage encoding human IgG). Immunoreactivity to multiple antigens was detected in the individual population sampled (i.e., individuals with castrate-resistant metastatic prostate cancer) that was absent in the sera of 25 healthy male blood donors (FIG. 2A-H). Of the 125 antigens evaluated, median antibody responses to 27 (22%) antigens were significantly higher in the sera of individuals with prostate cancer compared with controls ($p<0.05$, Wilcoxon Rank Sum test, FIG. 2A-H). Of these 27 antigens, 22 were previously identified in individuals with chronic prostatitis.

Antibody Responses to Antigens of the Antigen Panel are Evident in Individuals with Early and Late Stages of Prostate Cancer and in Individuals with Prostatitis.

To determine if recognition of particular antigens distinguishes individuals with prostate cancer from individuals with prostatitis or from men without known prostate disease, sera from a larger population of healthy male control blood donors (n=53), individuals with chronic prostatitis (n=45), and individuals with different stages of prostate cancer (n=126) were analyzed. Serum samples were obtained from men with newly diagnosed prostate cancer (pre-treatment, n=18), individuals with treated disease and no evidence of recurrence (n=32), individuals with metastatic disease responsive to androgen deprivation therapy (n=44), and additional individuals with castrate-resistant metastatic disease (n=32). In addition, the panel of antigens was modified to exclude two antigens (Pro39 and ADT28) not immunologically recognized in the initial screen, and to include phage containing genes that encoded three additional antigens (Mad-Pro-30, SEQ ID NO: 30; Mad-Pro-34, SEQ ID NO: 34; and the androgen receptor ligand-binding domain, SEQ ID NO:129) that had previously been identified as immunologically recognized antigens (Dunphy et al., 2004 supra; Olson and McNeel, 2007 supra). To account for background reactivity of individual membranes and variability in plaque immunoreactivity, each of the replicate individual plaques was visually scored as immunoreactive or not.

Figures 3A, 3B, 3C, 3D, 3E, 3F:
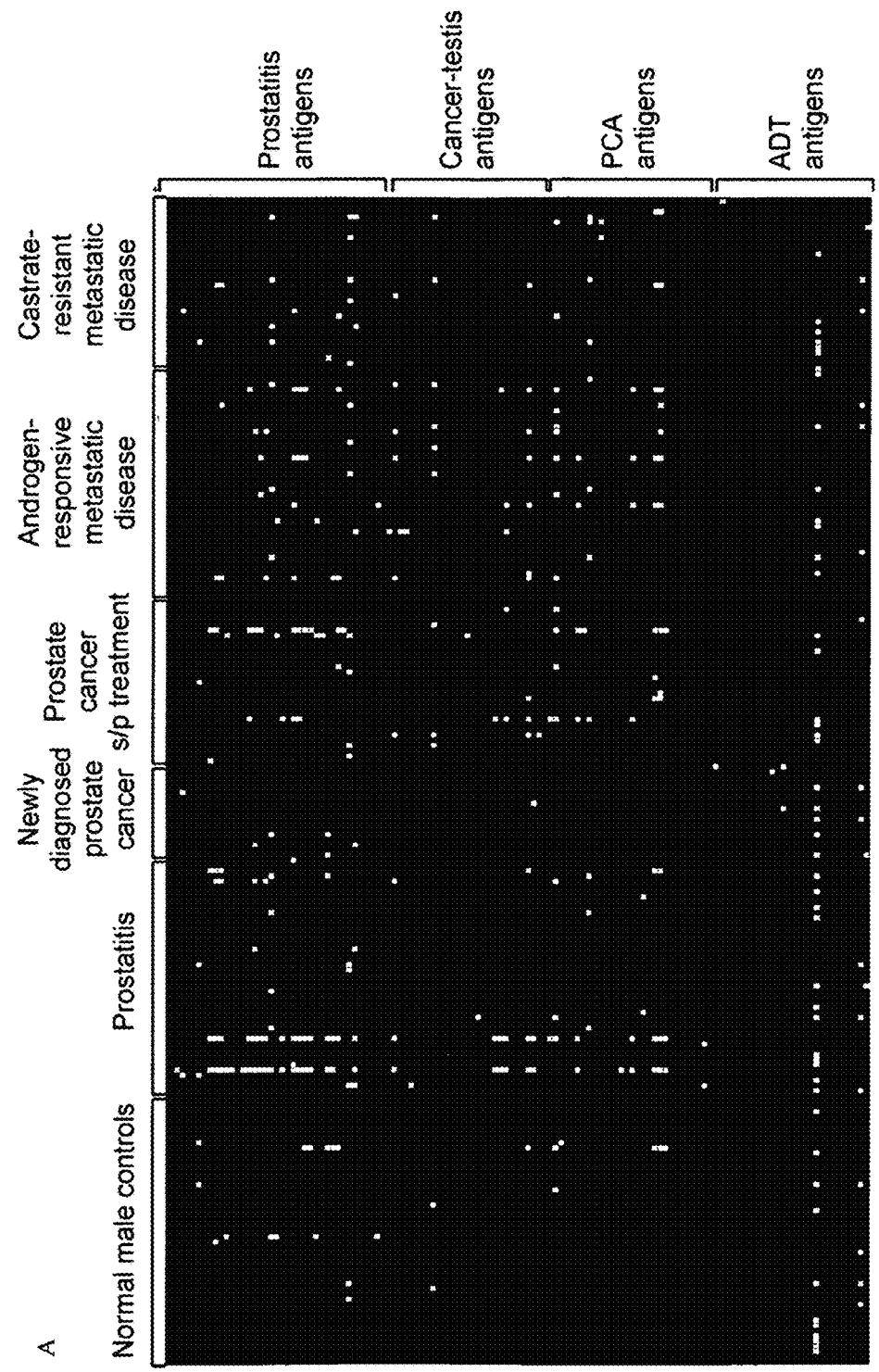
FIGS. 3A-3F illustrate immunoreactivity of individuals with early and late stages of prostate cancer.

As demonstrated in FIG. 3A, immunoreactivity to multiple antigens was identified. FIG. 3A shows a heatmap depicting relative immunoreactivity for each antigen, grouped by the study from which the antigens were originally identified, and for each individual or control group. Spots are graded in color intensity from 3 of 3 replicates visually immunoreactive (white), to 2 of 3 (grey), to not immunoreactive (black). Overall, however, responses to at least one antigen were not more frequently observed in the individual population (72/126, 57%) or prostatitis population (28/45, 62%) compared with the control population (22/53, 42%; p=0.11 and p=0.08, respectively). We identified no single antigen to which immunoreactivity was significantly more frequent in the individual population than in the control population. Instead, 23 antigens with high (>4) positive likelihood ratio values were identified based on a ROC analysis of IgG responses to antigens among prostate cancer individual samples compared to control individual samples (Table II). FIG. 3B-F shows a subset analysis for the 23 antigens with the highest positive likelihood ratio values when comparing prostate cancer cases to normal control cases.

TABLE II

One embodiment of the antigen panel. Shown is the subset of lambda phage-encoded antigens with the highest specificity for prostate cancer based on receiver operating curve analysis (see also FIG. 3B-F). Antigens with a positive likelihood ratio > 4 (sensitivity/(1-specificity)) are included, and the positive likelihood ratio is shown.

| Designation | Positive Likelihood Ratio | SEQ ID NO: | Gene name |
|---|---|---|---|
| ADT14 | ∞ | 114 | Chromosome 16 gene contig |
| CTA3 | ∞ | 44 | NY-ESO-1 |
| CTA23 | ∞ | 64 | Mage A4 |
| PCA6 | ∞ | 76 | Matrix metallopeptidase 24 |
| PCA 8 | ∞ | 78 | Prolactin-induced protein |
| PCA 10 | ∞ | 80 | Mannose-6-phosphate receptor binding protein 1 |
| PCA 16 | ∞ | 86 | PAP-associated domain |
| PRO5 | ∞ | 5 | hRPK.209-J-20 DNA from chromosome 17 |
| PRO 10 | ∞ | 10 | Macrophage capping protein gelsolin-like (CAPG) |
| PRO 12 | ∞ | 12 | BAC C-2506P8 from chromosome 14 |
| PRO 17 | ∞ | 17 | Dual specificity phosphatase 12 |
| PRO 18 | ∞ | 18 | Protein kinase A anchor protein 13/lymphoid blast crisis oncogene/breast cancer nuclear receptor-binding auxiliary protein (BRX) |
| PRO 19 | ∞ | 19 | BAC RP11-752K22 from chromosome 2 |
| PRO 20 | ∞ | 20 | Frizzled-1 |
| PRO 24 | ∞ | 24 | Adducin 1 |
| PRO 25 | ∞ | 25 | RP11-3J10 on chromosome 9 |
| PRO 35 | ∞ | 35 | BAC RP11-321G3 |
| CTA27 | 8.4 | 68 | Mage A3 |
| PCA 21 | 8.4 | 91 | Plexin B2 |

TABLE II-continued

One embodiment of the antigen panel. Shown is the subset of lambda phage-encoded antigens with the highest specificity for prostate cancer based on receiver operating curve analysis (see also FIG. 3B-F). Antigens with a positive likelihood ratio > 4 (sensitivity/(1-specificity)) are included, and the positive likelihood ratio is shown.

| Designation | Positive Likelihood Ratio | SEQ ID NO: | Gene name |
|---|---|---|---|
| PRO 40 | 6.7 | 40 | Recombination signal binding protein (RBPJK) |
| PCA 2 | 5.5 | 72 | Ribosomal protein L7a |
| PRO 34 | 5.4 | 34 | Pituitary tumor-transforming 1 interacting protein |
| PRO 32 | 4.2 | 32 | RP11-746L20 DNA from chromosome 8 |

Antibody Responses to Prostate Tissue-Associated Antigens Occur Irrespective of the Stage of Prostate Cancer.

Figure 4A:
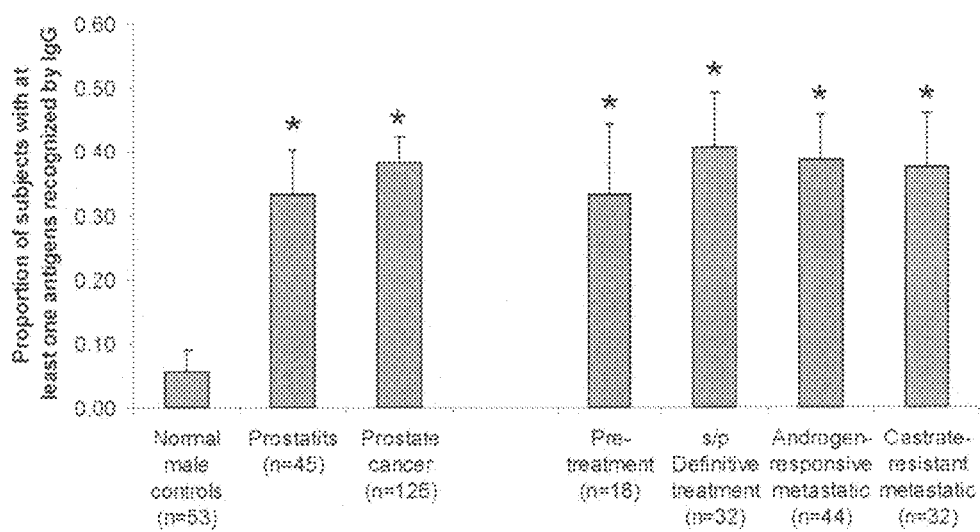
FIGS. 4A-4B illustrate the proportion and standard error of subjects in each population recognizing at least one (FIG. 4A) or at least three (FIG. 4B) of the antigens identified in Table II. Asterisks denote higher frequency compared to control population.
Figure 4B:
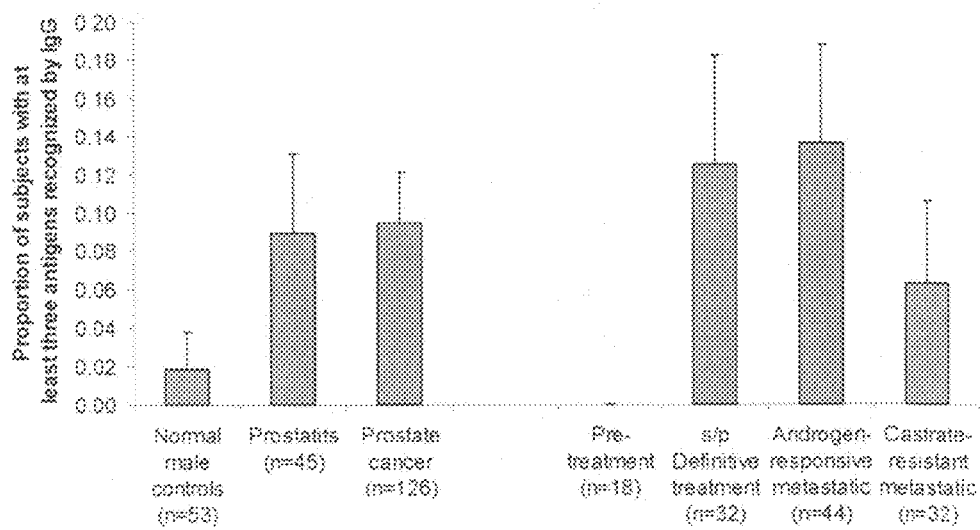

FIG. 4 shows the proportion and standard error of subjects in each population recognizing at least one (FIG. 4A) or at least three (FIG. 4B) of the antigens identified in Table II. Asterisks denote higher frequency compared to the control population (p<0.05, computed by logistic regression analysis and Dunnett's method for multiple comparisons). A subset analysis showed that the proportion of individuals with a detectable antibody response to at least one of the 23 antigens was significantly higher in the prostate cancer individual population when compared to the control population (FIG. 4A), that is, 48/126 (38%) versus 3/53 (6%) (p<0.001). Antibody responses detected in sera from prostatitis individuals (15/45, 33%) were significantly higher than those detected in the control population (p=0.003). Antibody responses detected in sera from prostatitis individuals were not significantly different from those detected in the prostate cancer individual population (FIG. 4A). As shown in FIG. 4B, the presence of immunoreactivity to three or more of the 23 antigens was more frequent in individuals with prostate cancer (12/126, 10%) and individuals with prostatitis (4/45, 9%) relative to male control blood donors (1/53, 2%).

Antibody Responses to Prostate-Associated Antigens are Uncommon in Sera from Male Individuals with Non Prostate Malignancies.

Figure 5:
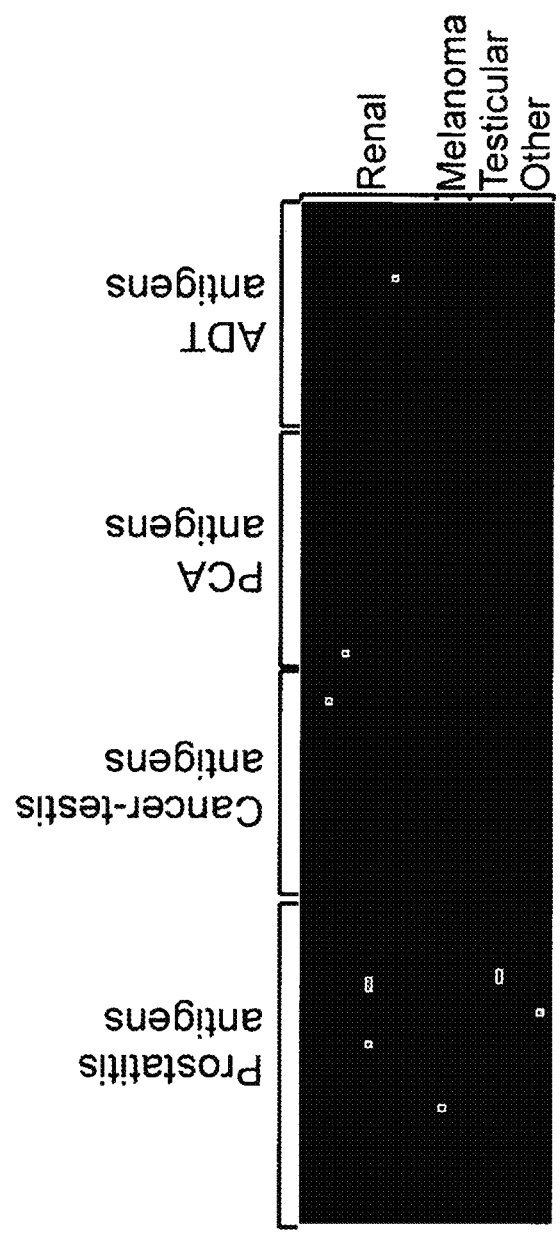
FIG. 5: shows a heatmap of the immunoreactivity for individual antigens among sera samples from male patients with non-prostate tumors. A white spot indicates a positive score.

The majority of antigens recognized by prostate cancer and prostatitis individuals are not prostate-specific in terms of expression, suggesting that the responses detected could be signatures of non-prostate-specific inflammatory conditions. To test this possibility, antibody responses to a panel of 126 antigens were evaluated using sera obtained from male individuals (n=31) with other non-prostate cancers (renal cell cancer, n=17; testicular cancer, n=5; melanoma, n=4; head and neck cancer, n=1; GI stromal tumor, n=1; bladder cancer, n=1; non-small cell lung cancer, n=1; carcinoid tumor n=1). FIG. 5 shows a heatmap depicting immunoreactivity for each antigen, grouped by the study from which they were originally identified, and for each individual tumor type. Spots were scored positive (white) if visually immunoreactive in at least 2 of 3 replicates. As shown in FIG. 5, while antibody responses were detectable to at least one of the 126 antigens in 7/31 sera samples (23%), only one response in 1/31 sera samples (3%) was detected to one of the 23 prioritized antigens. This result was not statistically different in frequency from responses identified in the non-cancer control population. The one response identified was to the Pro32 antigen, which exhibited the lowest positive likelihood ratio (Table II).

Discussion

Antigenic Targets of a Prostate-Associated Immune Response are Recognized in Populations of Individuals with Prostatitis and Prostate Cancer.

Immune responses to antigens originally identified in individuals with chronic prostatitis are also recognized in individuals with advanced prostate cancer relative to controls, suggesting that many "prostatitis antigens" represent true immunologically recognized antigens of the prostate, many of which coincide with antibody recognition in individuals with prostate cancer. Specific antibody responses to at least one member of a subset of 23 of these antigens were detectable in sera of individuals with prostate cancer or clinical prostatitis, but were rare in sera from male subjects with other types of cancer and in male subjects without prostate cancer or prostatitis.

These results, while not suggesting causality, suggest an association between chronic inflammatory conditions, such as prostatitis, and prostate cancer, or at least suggest that targets of a prostate-associated immune response can be recognized in these disorders. These results further suggest that the prostate expresses a set of antigens recognized immunologically by multiple individuals. The evaluation of antibody responses to prostate-associated antigens can potentially identify individuals in a premalignant inflammatory state at risk for developing prostate cancer. To further test this potential, sera obtained from individuals without a history of prostatitis but who developed prostate cancer within several years can be screened using the set of antigens identified herein.

Advantages of the phage immunoblot approach described here are the ease of transfection and protein expression in bacteria, particularly for novel proteins for which there are no available reagents, and the ability to simultaneously evaluate antibody responses to multiple antigens simultaneously from a single sample.

It is understood that certain adaptations of the invention described in this disclosure are a matter of routine optimization for those skilled in the art, and can be implemented without departing from the spirit of the invention, or the scope of the appended claims. All publications and patents mentioned in the above specification are herein incorporated by reference. Various modifications and variations of the described method and system of the invention will be apparent to those skilled in the art without departing from the scope and spirit of the invention. It is understood, however, that examples and embodiments of the present invention set forth above are illustrative and not intended to confine the invention. The invention embraces all modified forms of the examples and embodiments as come with the scope of the following claims.

---

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10191056B2). An electronic copy of the "Sequence Listing" will also be available from the USPTO upon request and payment of the fee set forth in 37 CFR 1.19(b)(3).

---

We claim:

1. An antigen panel for identifying immunoreactivity associated with a premalignant or malignant prostate, the panel comprising antigens encoded by SEQ ID NO:5, SEQ ID NO:10, SEQ ID NO:12, SEQ ID NO:17, SEQ ID NO:18, SEQ ID NO:19, SEQ ID NO:20, SEQ ID NO:24, SEQ ID NO:25, SEQ ID NO:32, SEQ ID NO:34, SEQ ID NO:35, SEQ ID NO:40, SEQ ID NO:44, SEQ ID NO:64, SEQ ID NO:68, SEQ ID NO:72, SEQ ID NO:76, SEQ ID NO:78, SEQ ID NO:80, SEQ ID NO:86, and SEQ ID NO:91, the encoded antigens being immobilized on one of a membrane, a plate, and a filter, and having a positive likelihood ratio of at least 4.

2. The panel of claim 1, wherein the panel further comprises an antigen encoded by a nucleic acid having a sequence selected from the group consisting of SEQ ID Nos: 1-4, 6-9, 11, 13-16, 21-23, 26-31, 33, 36-39, 31-43, 45-63, 65-67, 69-71, 73-75, 77, 79, 81-85, 87-90, and 92-128.

3. The panel of claim 1, the panel consisting of antigens encoded by SEQ ID NO:5, SEQ ID NO:10, SEQ ID NO:12, SEQ ID NO:17, SEQ ID NO:18, SEQ ID NO:19, SEQ ID NO:20, SEQ ID NO:24, SEQ ID NO:25, SEQ ID NO:32, SEQ ID NO:34, SEQ ID NO:35, SEQ ID NO:40, SEQ ID NO:44, SEQ ID NO:64, SEQ ID NO:68, SEQ ID NO:72, SEQ ID NO:76, SEQ ID NO:78, SEQ ID NO:80, SEQ ID NO:86, and SEQ ID NO:91.

4. The panel of claim 1, wherein at least three of the antigens in the panel elicit an immune response in at least about 9% of individuals with prostatitis or prostate cancer.

5. The panel of claim 1, wherein each antigen is expressed by a phage and attached to the membrane, plate or filter via the phage.

6. The panel of claim 1, wherein the plate is a multi-well plate.

* * * * *

UNITED STATES PATENT AND TRADEMARK OFFICE
CERTIFICATE OF CORRECTION

PATENT NO.        : 10,191,056 B2
APPLICATION NO.   : 14/757607
DATED             : January 29, 2019
INVENTOR(S)       : Douglas G. McNeel and Brett B. Maricque Page 1 of 1

It is certified that error appears in the above-identified patent and that said Letters Patent is hereby corrected as shown below:

In the Specification

In Column 3, Line 47, the second CTA5 should be --CTA8--

In Column 6, Line 20, the second CTA5 should be --CTA8--

In Column 6, Line 43, PRO5 should be --PRO8--

In Column 6, Line 43, PROM should be --PRO11--

Signed and Sealed this
Sixth Day of August, 2019

Andrei Iancu
*Director of the United States Patent and Trademark Office*